US008454956B2

(12) United States Patent
Chang

(10) Patent No.: US 8,454,956 B2
(45) Date of Patent: *Jun. 4, 2013

(54) METHODS FOR TREATING RHEUMATOID ARTHRITIS AND OSTEOPOROSIS WITH ANTI-IL-20 ANTIBODIES

(75) Inventor: Ming-Shi Chang, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/869,224

(22) Filed: Aug. 26, 2010

(65) Prior Publication Data

US 2011/0064731 A1    Mar. 17, 2011

Related U.S. Application Data

(60) Provisional application No. 61/238,661, filed on Aug. 31, 2009.

(51) Int. Cl.
*A61K 39/395*    (2006.01)

(52) U.S. Cl.
USPC ............... 424/130.1; 424/139.1; 424/133.1

(58) Field of Classification Search
None
See application file for complete search history.

(56) References Cited

U.S. PATENT DOCUMENTS

| | | | |
|---|---|---|---|
| 5,585,089 A * | 12/1996 | Queen et al. ............. | 424/133.1 |
| 5,605,690 A | 2/1997 | Jacobs et al. | |
| 5,888,510 A * | 3/1999 | Kishimoto et al. ........ | 424/141.1 |
| 7,119,191 B2 | 10/2006 | Conklin et al. | |
| 7,122,632 B2 | 10/2006 | Foster et al. | |
| 7,151,166 B2 | 12/2006 | Conklin et al. | |
| 7,393,684 B2 | 7/2008 | Xu et al. | |
| 7,435,800 B2 | 10/2008 | Chang | |
| 7,611,705 B2 * | 11/2009 | Chang ...................... | 424/141.1 |
| 7,786,274 B2 | 8/2010 | Chang | |
| 7,837,994 B2 | 11/2010 | Chang | |
| 8,206,712 B2 | 6/2012 | Chang | |
| 8,287,861 B2 | 10/2012 | Pass et al. | |
| 2002/0151532 A1 | 10/2002 | Kagan et al. | |
| 2003/0148955 A1 | 8/2003 | Plenneke | |
| 2004/0009168 A1 | 1/2004 | Kaisheva et al. | |
| 2004/0191243 A1 | 9/2004 | Chen et al. | |
| 2004/0197324 A1 | 10/2004 | Liu et al. | |
| 2004/0235728 A1 | 11/2004 | Stoch et al. | |
| 2004/0235808 A1 | 11/2004 | Wang | |
| 2005/0003475 A1 | 1/2005 | Foster et al. | |
| 2005/0136004 A1 | 6/2005 | Xu et al. | |
| 2005/0143333 A1 | 6/2005 | Richards et al. | |
| 2006/0134756 A1 | 6/2006 | Xu et al. | |
| 2006/0142550 A1 | 6/2006 | Chang | |
| 2006/0177447 A1 | 8/2006 | Xu | |
| 2006/0188476 A1 | 8/2006 | Olsen et al. | |
| 2006/0269551 A1 | 11/2006 | Thompson et al. | |
| 2007/0053871 A1 | 3/2007 | Li et al. | |
| 2007/0116700 A1 | 5/2007 | Liu et al. | |
| 2008/0247945 A1 | 10/2008 | Xu et al. | |
| 2009/0312236 A1 | 12/2009 | Beals et al. | |
| 2011/0091475 A1 | 4/2011 | Pass et al. | |

FOREIGN PATENT DOCUMENTS

| | | |
|---|---|---|
| WO | WO 92/07584 A1 | 5/1992 |
| WO | WO 99/03982 A1 | 1/1999 |
| WO | WO 99/27103 A1 | 6/1999 |
| WO | WO 01/46261 A1 | 6/2001 |
| WO | WO 03/051384 A1 | 6/2003 |
| WO | WO 2004/085475 A2 | 10/2004 |
| WO | WO 2005/052000 A2 | 6/2005 |
| WO | WO 2006/086396 A2 | 8/2006 |
| WO | WO 2007/081465 A2 | 7/2007 |
| WO | WO 2008/009545 A1 | 1/2008 |
| WO | WO 2008/009645 A1 | 1/2008 |
| WO | WO 2008/045563 A2 | 4/2008 |
| WO | WO 2008/086395 A2 | 7/2008 |
| WO | WO 2008/157161 A1 | 12/2008 |
| WO | WO 2009/077483 A1 | 6/2009 |
| WO | WO 2009/103113 A1 | 8/2009 |
| WO | WO 2010/000721 A1 | 1/2010 |
| WO | WO 2010/072691 A1 | 7/2010 |
| WO | WO 2011/104381 A2 | 9/2011 |
| WO | WO 2011/147921 A1 | 12/2011 |

OTHER PUBLICATIONS

Chuntharapai et al (1997), Methods in Enzymology, vol. 288, pp. 15-27.*
Hsu Y.H. et al., "Function of Interleukin-20 as a proinflammatory molecule in rheumatoid and experimental arthritis", Arthritis and Rheumatism, vol. 54(9), pp. 2722-2733 (Sep. 2006).
Hsieh M.Y. et al., "Interleukin-20 promotes angiogenesis in a direct and indirect manner", Genes and Immunity, vol. 7(3), pp. 234-242 (Apr. 2006).
Wei C.C. et al., "IL-20: Biological functions and clinical implications", Journal of Biomedical Science, vol. 13(5), pp. 601-612 (May 16, 2006).
Sabat R. et al., "IL-19 and IL-20: Two novel cytokines with importance in inflammatory diseases", Expert Opinion on Therapeutic Targets, vol. 11(5), pp. 601-612 (May 2007).
Wei C.C. et al., "Detection of IL-20 and its receptors on psoriatic skin", *Clinical Immunology*, vol. 117(1), pp. 65-72 (Oct. 2005).
Chen, W-Y et al. (2009) "IL-20 is Regulated by Hypoxia-inducible Factor and Up-Regulated After Experimental Ischemic Stroke," *Journal of Immunology* 182:5003-5012.

(Continued)

*Primary Examiner* — Prema Mertz
(74) *Attorney, Agent, or Firm* — Wolf, Greenfield & Sacks, P.C.

(57) ABSTRACT

The invention features methods and compositions for preventing or treating rheumatoid arthritis and osteoporosis by administering an antagonist of IL-20. The IL-20 antagonist may be an anti-IL-20 antibody, such as mAB 7E, that is capable of binding human IL-20 and blocking IL-20 interaction with its receptors.

13 Claims, 12 Drawing Sheets

OTHER PUBLICATIONS

GenBank Accession No. AAK84423.1, last updated Aug. 9, 2001, located at http://www.ncbi.nim.nih.gov/protein/15128211, last visited on Jan. 14, 2010, one page.

Hunt, D.W.C. et al. (Sep./Oct. 2006), "Ultraviolet B Light Stimulates Interleukin-20 Expression by Human Epithelial Keratinocytes," *Photochemistry and Photobiology* 82:1292-1300.

International Search Report mailed on Dec. 19, 2007, for PCT Application No. PCT/US06/46802, filed on Dec. 7, 2006, five pages.

International Search Report mailed on Feb. 18, 2010, for PCT Application No. PCT/US2009/059872, filed on Oct. 7, 2009, five pages.

International Search Report mailed on Feb. 24, 2010, for PCT Application No. PCT/US09/59865, filed on Oct. 7, 2009, five pages.

Mayo Clinic, (Jul. 8, 2008), "Stroke, Treatment and Drugs" located at http://www.MayoClinic.com, last visited on Sep. 29, 2009, three pages.

Mayo Clinic, (2001-2009), "Stroke," located at http://www.MayoClinic.com, last visited on Sep. 29, 2009, two pages.

Written Opinion mailed on Dec. 19, 2007, for PCT Application No. PCT/US06/46802, filed on Dec. 7, 2006, four pages.

Written Opinion mailed on Feb. 18, 2010, for PCT Application No. PCT/US2009/059872, filed on Oct. 7, 2009, six pages.

Written Opinion mailed on Feb. 24, 2010, for PCT Application No. PCT/US09/59865, filed on Oct. 7, 2009, five pages.

Goffe et al., Etanercept: An overview. J Am Acad Dermatol. Aug. 2003;49(2 Suppl):S105-11.

Beiboer et al., Guided selection of a pan carcinoma specific antibody reveals similar binding characteristics yet structural divergence between the original murine antibody and its human equivalent. J Mol Biol. Feb. 25, 2000;296(3):833-49.

Blumberg et al., Interleukin 20: discovery, receptor identification, and role in epidermal function. Cell. Jan. 12, 2001;104(1):9-19.

Chang et al., Crystal structure of interleukin-19 defines a new subfamily of helical cytokines. J Biol Chem. Jan. 31, 2003;278(5):3308-13. Epub Oct. 25, 2002.

Cunningham et al., High-resolution epitope mapping of hGH-receptor interactions by alanine-scanning mutagenesis. Science. Jun. 2, 1989;244(4908):1081-5.

D'Andrea et al., Interleukin 10 (IL-10) inhibits human lymphocyte interferon gamma-production by suppressing natural killer cell stimulatory factor/IL-12 synthesis in accessory cells. J Exp Med. Sep. 1, 1993;178(3):1041-8.

Dumont, IL-10-related cellular cytokines and their receptors: new targets for inflammation and cancer therapy. Expert Opin Ther Patents. Mar. 2004;14(3):281-99.

Dumoutier et al., Cutting edge: STAT activation by IL-19, IL-20 and mda-7 through IL-20 receptor complexes of two types. J Immunol. Oct. 1, 2001;167(7):3545-9.

Egermann et al., Direct adenoviral transfer of bone morphogenetic protein-2 cDNA enhances fracture healing in osteoporotic sheep. Hum Gene Ther. May 2006;17(5):507-17.

EST From Incyte Pharmaceuticals Inc., INC819592. 1996. 1 page.

George et al., Current Methods in Sequence Comparison. Macromolecular Sequencing and Synthesis. 1988;127-49.

Harlow et al., Antibodies A Laboratory Manual. Cold Springs Harbor Laboratory. 1988;76.

Hsu et al., Anti-IL-20 monoclonal antibody inhibits the differentiation of osteoclasts and protects against osteoporotic bone loss. J Exp Med. Aug. 29, 2011;208(9):1849-61. Epub Aug. 15, 2011.

Hsu et al., Function of interleukin-20 as a proinflammatory molecule in rheumatoid and experimental arthritis. Arthritis Rheum. Sep. 2006;54(9):2722-33.

Incyte Pharmaceuticals Inc., INC4304592, Jul. 8, 1998. 1 page.

Klimka et al., Human anti-CD30 recombinant antibodies by guided phage antibody selection using cell panning. Br J Cancer. Jul. 2000;83(2):252-60.

Kragstrup et al., The expression of IL-20 and IL-24 and their shared receptors are increased in rheumatoid arthritis and spondyloarthropathy. Cytokine. Jan. 2008;41(1):16-23. Epub Dec. 3, 2007.

Li et al., Interleukin-20 induced cell death in renal epithelial cells and was associated with acute renal failure. Genes Immun. Jul. 2008;9(5):395-404. Epub May 22, 2008.

Lonberg, Human monoclonal antibodies from transgenic mice. Handbook Exp Phannacol. 2008;(181):69-97.

Mikayama et al., Molecular cloning and functional expression of a cDNA encoding glycosylation-inhibiting factor. Proc Natl Acad Sci U S A. Nov. 1, 1993;90(21):10056-60.

Otkjaer et al., The dynamics of gene expression of interleukin-19 and interleukin-20 and their receptors in psoriasis. Br J Dermatol. Nov. 2005;153(5):911-8.

Parrish-Novak et al., Interleukins 19, 20, and 24 signal through two distinct receptor complexes. Differences in receptor-ligand interactions mediate unique biological functions. J Biol Chem. Dec. 6, 2002;277(49):47517-23. Epub Sep. 25, 2002.

Parrish-Novak et al., Overlapping Ligand Specificities but Divergent Function in the IL-20 Sub family. J Interferon Cytokine Res. 2002;22. Supplement 46.

Rich, IL-20: a new target for the treatment of inflammatory skin disease. Expert Opin Ther Targets. Apr. 2003;7(2):165-74.

Rohovsky et al., Groth Factors and Angiogenesis in Wound Healing. Growth Factors Wound Healing. Ziegler et al., eds. 1997:8-26.

Romer et al., Epidermal overexpression of interleukin-19 and -20 mRNA in psoriatic skin disappears after short-term treatment with cyclosporine a or calcipotriol. J Invest Dermatol. Dec. 2003;121(6):1306-11.

Saidenberg-Kermanac'h et al., TNF-alpha antibodies and osteoprotegerin decrease systemic bone loss associated with inflammation through distinct mechanisms in collagen-induced arthritis. Bone. Nov. 2004;35(5):1200-7.

Salinas et al., Understanding and modulating opalescence and viscosity in a monoclonal antibody formulation. J Pharm Sci. Jan. 2010;99(1):82-93.

Seriolo et al., Bone metabolism changes during anti-TNF-alpha therapy in patients with active rheumatoid arthritis. Ann N Y Acad Sci. Jun. 2006;1069:420-7.

Siderov et al., Care with intrathecal trastuzumab. Lancet Oncology. 2006;7(11):888.

Slavin, Cytokines and Tissue Repair. J Immunol Immunopharmacol. 1997;17(1):25-9.

Staelens et al., Humanization by variable domain resurfacing and grafting on a human IgG4, using a new approach for determination of non-human like surface accessible framework residues based on homology modelling of variable domains. Mol Immunol. Mar. 2006;43(8):1243-57. Epub Aug. 22, 2005.

Stenderup et al., Interleukin 20 Controls Psoriasis Induction and Maintenance. British Journal of Dermatology. 2006;154:11-35.

Stenderup et al., Interleukin-20 plays a critical role in maintenance and development of psoriasis in the human xenograft transplantation model. Br J Dermatol. Feb. 2009;160(2):284-96. Epub Oct. 20, 2008.

Voet et al., Biochemistry. John Wiley & Sons, Inc. New York. 1990:126-8, 228-34.

Wang et al., Prominent production of IL-20 by CD68+/CD1 1c+ myeloid-derived cells in psoriasis: Gene regulation and cellular effects. J Invest Dermatol. Jul. 2006;126(7):1590-9. Epub Apr. 27, 2006.

Wuyts et al., Isolation of the CXC chemokines ENA-78, GRO alpha and GRO gamma from tumor cells and leukocytes reveals NH2-terminal heterogeneity. Functional comparison of different natural isoforms. Eur J Biochem. Mar. 1999;260(2):421-9.

Zheng et al., Role of cytokine therapy in the treatment of psoriasis. Drug Discov Today: Ther Strat. 2007;4(1):25-31.

\* cited by examiner

SEQUENCE LISTING

<160> NUMBER OF SEQ ID NOS: 6

<210> SEQ ID NO 1
<211> LENGTH: 363
<212> TYPE: DNA
<213> ORGANISM: Artificial sequence
<220> FEATURE:
<223> OTHER INFORMATION: DNA encoding mAb 7E heavy chain variable region

<400> SEQUENCE: 1

```
gaattgaagc ttgaggagtc tggaggaggc ttggtgcagc ctggaggatc catgaaactc      60
tcttgtgctg cctctggatt cactttagt gacgcctgga tggactgggt ccgccagtct     120
ccagagaagg ggcttgagtg gattgctgaa attagaagca aagctaataa ttatgcaaca     180
tactttgctg agtctgtgaa agggaggttc accatctcaa gagatgattc caaaagtggt     240
gtctacctgc aaatgaacaa cttaagagct gaggacactg gcatttattt ctgtaccaag     300
ttatcactac gttactggtt cttcgatgtc tggggcgcag ggaccacggt caccgtctcc     360
tca                                                                   363
```

<210> SEQ ID NO 2
<211> LENGTH: 121
<212> TYPE: PRT
<213> ORGANISM: Artificial sequence
<220> FEATURE:
<223> OTHER INFORMATION: mAb 7E heavy chain variable region

<400> SEQUENCE: 2

```
Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
            100                 105                 110
```

Ala Gly Thr Thr Val Thr Val Ser Ser
            115                 120

<210> SEQ ID NO 3
<211> LENGTH: 339
<212> TYPE: DNA
<213> ORGANISM: Artificial sequence
<220> FEATURE:
<223> OTHER INFORMATION: DNA encoding mAb 7E light chain variable region

<400> SEQUENCE: 3
gattttgtga tgacccagac tccactcact ttgtcggtta ccattggaca accagcctcc      60
atctcttgca agtcaagtca gagcctcttg atagtgatg gaaagacata tttgaattgg     120
ttgttacaga ggccaggcca gtctccaaag cacctcatct atctggtgtc taaactggac     180
tctggagtcc ctgacaggtt cactggcagt ggatcaggga ccgatttcac actgagaatc     240
agcagagtgg aggctgagga tttgggagtt tattattgct ggcaaagtac acattttccg     300
tggacgttcg gtggaggcac caagctggaa atcaaacgg                            339

<210> SEQ ID NO 4
<211> LENGTH: 112
<212> TYPE: PRT
<213> ORGANISM: Artificial sequence
<220> FEATURE:
<223> OTHER INFORMATION: mAb 7E light chain variable region

<400> SEQUENCE: 4

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

<210> SEQ ID NO 5
<211> LENGTH: 161
<212> TYPE: PRT
<213> ORGANISM: Homo sapiens

<400> SEQUENCE: 5

Ala Gln Val Ala Phe Thr Pro Tyr Ala Pro Glu Pro Gly Ser Thr Cys
1               5                   10                  15

Arg Leu Arg Glu Tyr Tyr Asp Gln Thr Ala Gln Met Cys Cys Ser Lys
            20                  25                  30

Cys Ser Pro Gly Gln His Ala Lys Val Phe Cys Thr Lys Thr Ser Asp
        35                  40                  45

Thr Val Cys Asp Ser Cys Glu Asp Ser Thr Tyr Thr Gln Leu Trp Asn
    50                  55                  60

Trp Val Pro Glu Cys Leu Ser Cys Gly Ser Arg Cys Ser Ser Asp Gln
65                  70                  75                  80

```
                                      -continued

Val Glu Thr Gln Ala Cys Thr Arg Glu Gln Asn Arg Ile Cys Thr Cys
                85                  90                  95

Arg Pro Gly Trp Tyr Cys Ala Leu Ser Lys Gln Glu Gly Cys Arg Leu
            100                 105                 110

Cys Ala Pro Leu Arg Lys Cys Arg Pro Gly Phe Gly Val Ala Arg Pro
        115                 120                 125

Gly Thr Glu Thr Ser Asp Val Val Cys Lys Pro Cys Ala Pro Gly Thr
    130                 135                 140

Phe Ser Asn Thr Thr Ser Ser Thr Asp Ile Cys Arg Pro His Gln Ile
145                 150                 155                 160

Cys

<210> SEQ ID NO 6
<211> LENGTH: 176
<212> TYPE: PRT
<213> ORGANISM: Homo sapiens

<400> SEQUENCE: 6

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

METHODS FOR TREATING RHEUMATOID ARTHRITIS AND OSTEOPOROSIS WITH ANTI-IL-20 ANTIBODIES

CROSS-REFERENCE TO RELATED APPLICATIONS

This application claims the benefit of U.S. Application Ser. No. 61/238,661, filed Aug. 31, 2009, entitled "Use of Anti-IL-20 Antibody for Treating Rheumatoid Arthritis and Osteoporosis", the contents of which are incorporated herein by reference.

FIELD OF INVENTION

The present invention relates to the use of an IL-20 antagonist for the prevention, delay of onset or treatment of rheumatoid arthritis and osteoporosis.

BACKGROUND OF THE INVENTION

Osteoporosis is a disease characterized by low bone mass and loss of bone tissue, resulting in weak and fragile bones. Net bone loss can be induced by various factors, e.g., low levels of estrogen, inadequate up take of calcium and vitamin D, and inflammation. Bone resorption is a major pathological factor in postmenopausal osteoporosis. Osteoporosis is a disorder of impaired bone strength that causes skeletal fragility and increases fracture risk (Theill, L E, et al. (2002) Annu Rev Immunol 20:795-823; Boyle, W J, et al. (2003) Nature 423; 337-342). Estrogen deficiency at menopause and androgen deficiency in men both cause an unbalanced increase in bone turnover, in which bone resorption exceeds bone formation. Relatively rapid bone loss occurs and is accompanied by the destruction of bone micro-architecture (Simonet, W S, et al. (1997) Cell 89:309-319; McClung, M, (2007) Arthritis Res Ther 9 Suppl 1:S3). In most instances, low bone mass is caused by an increase in the number of osteoclasts or by excessive osteoclast activity (Walsh, N C, et al. (2005) Immunol Rev 208:228-251). Osteoclasts are multinucleated giant cells that express tartrate-resistant acid phosphatase (TRAP) and calcitonin receptors. Osteoclast formation requires two factors: macrophage colony-stimulation factor (M-CSF) and the receptor activator of NF-κB ligand (RANKL) (Takayanagi, H, et al. (2005) Immunol Rev 208:181-193; Ross, F P & Teitelbaum, S L, (2005) Immunol Rev 208:88-105). M-CSF, which mediates the survival and proliferation of monocyte/macrophage precursors, is produced primarily by stromal fibroblasts, osteoblasts, and activated T cells. RANK, is the sole signaling receptor for RANKL, which induces the development and activation of osteoclasts (Suda, T, et al., (1999) Endocr Rev 20:345-357). The in vivo significance of the RANKL-RANK signaling pathway has been verified by observations that the deficiency of either gene in mice causes severe osteoporosis (increased bone mass) and the disappearance of osteoclasts (Kong, Y Y, et al., (1999) Nature 397:315-323; Li, J, et al., (2000) Proc Nati Acad Sci USA 97:1566-1571). Several proinflammatory cytokines, such as TNF-α, IL-1β, IL-15, IL-17, and IL-23, induce the multinucleation of osteoclast precursors, or their commitment to the osteoclast phenotype, and may act synergistically with RANKL (Feldmann, M, et al. (2001) Curr Dir Autoimmun 3:188-199; O'Gradaigh, D, et al. (2004) Ann Rheum Dis 63:354-359; Sato, K, et al., (2006) J Exp Med 203:2673-2682; Ju, J H, et al., (2008) J Immunol 181:1507-1518).

The pleiotropic inflammatory cytokine IL-20, a member of the IL-10 family—IL-10, IL-19, IL-20, IL-22, IL-24, and IL-26 (Blumberg, H, et al., (2001) Cell 104:9-19; Pestka, S, et al., (2004) Annu Rev Immunol 22:929-979)—is expressed in monocytes, epithelial cells, and endothelial cells. IL-20 acts on multiple cell types by activating a heterodimer receptor complex of either IL-20R1/IL-20R2 or IL-22R1/IL-20R2 (Dumoutier, L., et al., (2001) J Immunol 167:3545-3549). It is involved in various inflammatory diseases (Wei, C C, et al., (2006) J Biomed Sci 13:601-612), such as psoriasis (Blumberg, H, et al., (2001) Cell 104:9-19; Sa, S M, et al., (2007) J Immunol 178:2229-2240; Wei, C C, et al., (2005) Clin Immunol 117:65-72), rheumatoid arthritis (Hsu, Y H, et al., (2006) Arthritis Rheum 54:2722-2733), atherosclerosis (Caligiuri, G, et al. (2006) Arterioscler Thromb Vasc Biol 26:1929-1930; Chen, W Y, et al. (2006) Arterioscler Thromb Vasc Biol 26:2090-2095), ischemic stroke (Chen, W Y & Chang, M S, (2009) J Immunol 182:5003-5012), and renal failure (Li, H H, et al., (2008) Genes Immun 9:395-404). IL-20 is regulated by hypoxia and inflammatory stimuli such as IL-1β and LPS (Chen, W Y & Chang, M S, (2009) J Immunol 182:5003-5012; Otkjaer, K, et al., (2007) J Invest Dermatol). IL-20 has recently been reported (Heuze-Vourc'h, N, et al., (2005) Biochem Biophys Res Commun 333:470-475; Hsieh, M Y, et al., (2006) Genes Immun 7:234-242; Tritsaris, K, et al., (2007) Proc Natl Acad Sci USA 104:15364-15369) to have regulated angiogenesis. In experimental rheumatoid arthritis, IL-20 induces synovial fibroblasts to secrete MCP-1, IL-6, and IL-8, and it acts as a proinflammatory cytokine (Hsu, Y H, et al., (2006) Arthritis Rheum 54:2722-2733).

IL-20 has been shown to be involved in rheumatoid arthritis and IL-20 soluble receptors have been shown to block IL-20, which reduces the severity of collagen-induced arthritis (Hsu, Y H, et al., (2006) Arthritis Rheum 54:2722-2733). Therefore, IL-20 is a promoting factor during the progression of rheumatoid arthritis. Little is known, however, about the function of IL-20 in bone resorption, or about the function of IL-20 in RANKL-RANK signaling-mediated osteoclastogenesis.

SUMMARY OF THE INVENTION

The invention provides a method for treating, delaying the onset of, or preventing osteoporosis in an individual comprising administering to the individual an effective amount of an IL-20 antagonist.

The invention also provides a method for treating, delaying the onset of, or preventing rheumatoid arthritis in an individual comprising administering to the individual an effective amount of an IL-20 antagonist in conjunction with a TNFα antagonist (such as an etanercept polypeptide).

Any IL-20 antagonist described herein may be used to treat, delay the onset of, or prevent osteoporosis or rheumatoid arthritis. In some embodiments, the IL-20 antagonist is an anti-IL-20 antibody, such as mAb 7E or a functional equivalent thereof.

The details of one or more embodiments of the invention are set forth in the description below. Other features or advantages of the present invention will be apparent from the following drawings and detailed description of several embodiments, and also from the appending claims.

DETAILED DESCRIPTION OF THE INVENTION

Figure 1:
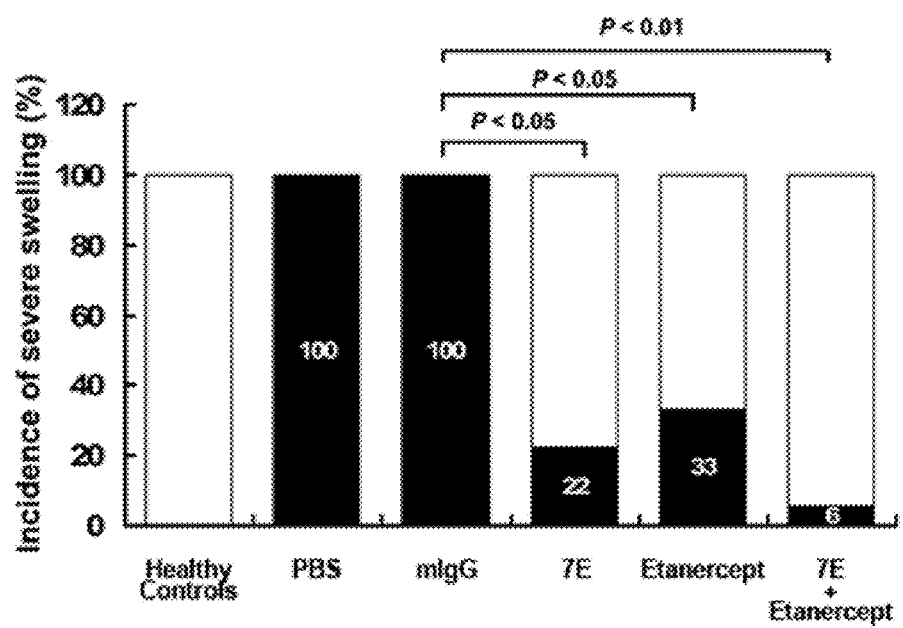
FIG. 1 is a chart showing the incidence of severe hind paw swelling in healthy rats and collagen-induced-arthritic rats treated with PBS, mIgG, mAb 7E, Etanercept, or both mAb 7E and Etanercept.

The present invention is based on the discovery that IL-20 is a novel osteoclastogenic cytokine that caused RANK expression on osteoclast precursors and RANKL expression on osteoblasts. Antagonists of IL-20; for example, the IL-20 specific monoclonal antibody mAb 7E, abolished IL-20-induced RANK and RANKL expression. These results showed that IL-20 antagonists may be used to inhibit osteoclast differentiation and protect individuals from osteoporotic bone loss in vivo. The invention is also based on the discovery that the IL-20 specific monoclonal antibody alone or combined with etanercept significantly reduced the severity of arthritis by decreasing hind-paw thickness and swelling, prevented cartilage damage and bone loss in an animal model for rheumatoid arthritis.

The invention provides methods of treating, delaying the onset of, or preventing osteoporosis in an individual by administering an effective amount of an IL-20 antagonist (such as an anti-IL-20 antibody or an antigen-binding fragment thereof). In some embodiments, the IL-20 antagonist is administered in combination with another therapeutic agent for osteoporosis. In some embodiments, the osteoporosis is post-menopausal osteoporosis. In some embodiments, the osteoporosis is associated with a hormone deficiency. For example, in some cases, the osteoporosis is associated with hormone ablation treatment. Examples of hormone ablation treatment include treatments of breast cancer and treatments of prostate cancer. In some embodiments, the osteoporosis is steroid-induced or steroid-associated osteoporosis. In some embodiments, the osteoporosis is associated with rheumatoid arthritis.

The invention also provides methods of treating, delaying the onset of, or preventing rheumatoid arthritis in an individual in need thereof by administering an effective amount of an IL-20 antagonist (such as an anti-IL-20 antibody or an antigen-binding fragment thereof) and an effective amount of a TNFα antagonist (such as an etanercept polypeptide).

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook, et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel, et al., eds., 1987); *PCR: The Polymerase Chain Reaction*, (Mullis, et al., eds., 1994); *Current Protocols in Immunology* (J. E. Coligan et al., eds., 1991); *Short Protocols in Molecular Biology* (Wiley and Sons, 1999); Immunobiology (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

Definitions

An "antibody" (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody."

Humanized antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

"Chimeric" antibodies refer to antibodies having a variable region or part of variable region from a first species and a constant region from a second species. Typically, in these chimeric antibodies, the variable region of both light and heavy chains mimics the variable regions of antibodies derived from one species of mammals, while the constant portions are homologous to the sequences in antibodies derived from another. In some embodiments, amino acid modifications can be made in the variable region and/or the constant region.

An antibody or a polypeptide that "specifically binds" or "binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target than it does with alternative targets. An antibody or a polypeptide "specifically binds" to a target if it binds with greater affinity, avidity, more readily, and/or with greater duration than it binds to other substances. For example, an antibody that specifically or preferentially binds to an IL-20 epitope is an antibody that binds this IL-20 epitope with greater affinity, avidity, more readily, and/or with greater duration than it binds to other IL-20 epitopes or non-IL-20 epitopes. It is also understood by reading this definition that, for example, an antibody (or moiety) that specifically binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, the term "IL-20" and refers to interleukin-20 and variants thereof that retain at least part of the activity of IL-20. As used herein, IL-20 includes all mammalian species of native sequence IL-20, including human, canine, feline, equine, or bovine.

An "IL-20 receptor" refers to one or more polypeptides that is bound by or activated by IL-20. In some cases, IL-20 binds to a complex formed by IL-20R1 and IL-20R2. In other cases, IL-20 binds to a complex formed by IL-20R2 and IL-22R1. As such, IL-20 receptors include IL-20R1, IL-20R2 and IL-22R1 of any mammalian species, including, but are not limited to, human, canine, feline, equine, primate, or bovine. Examples of human IL-20 receptors include hIL-20R1 (GenBank Accession No. NM_014432.2), hIL-20R2 (GenBank Accession No. NM_144717.2) and hIL-22R1 (NM_181309.1). Sequences of human IL receptors have been described; for example, in U.S. Pat. Nos. 6,610,286; 7,122,632; 7,393,684; and 7,537,761; and U.S. Pat. App. Pub. Nos. 2006/0263850 A1; 2006/0263851 A1; 2008/0247945 A1, and 2009/0074661 A1.

An "IL-20 antagonist" refers to any molecule that blocks, suppresses or reduces (including significantly) IL-20 biological activity, including downstream pathways mediated by IL-20 signaling, such as receptor binding and/or elicitation of a cellular response to IL-20. The term "antagonist" implies no specific mechanism of biological action whatsoever, and is deemed to expressly include and encompass all possible pharmacological, physiological, and biochemical interactions with IL-20 whether direct or indirect. Exemplary IL-20 antagonists include, but are not limited to, an anti-IL-20 antibody or fragment thereof, an anti-sense molecule directed to an IL-20 (including an anti-sense molecule directed to a nucleic acid encoding IL-20), a small interfering RNA (siRNA) directed toward an IL-20 nucleic acid, a microRNA directed toward an IL-20 nucleic acid, an IL-20 inhibitory compound. For purpose of the present invention, it will be explicitly understood that the term "antagonist" encompass all the previously identified terms, titles, and functional states and characteristics whereby the IL-20 itself, an IL-20 biological activity (including but not limited to its ability to mediate any aspect osteoporosis), or the consequences of the biological activity, are substantially nullified, decreased, or neutralized in any meaningful degree. In some embodiments, an IL-20 antagonist binds IL-20 and prevents IL-20 receptor complex formation. In other embodiments, an IL-20 antagonist inhibits or reduces IL-20 synthesis and/or production (release). Examples of types of IL-20 antagonists are provided herein.

As used herein, an "anti-IL-20 antibody" refers to an antibody which is able to bind to IL-20 and inhibit IL-20 biological activity and/or downstream pathway(s) mediated by IL-20 signaling.

The term "anti-IL-20 antibody 7E" refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent.

A "functional equivalent" of mAb 7E is an antibody that (1) specifically binds to human IL-20, and (2) contains a heavy chain variable region (VH) at least 70% (e.g., 80%, 90%, or 95%) identical to that of mAb 7E (shown below as SEQ ID NO: 2, encoded by the nucleotide sequence of SEQ ID NO:1) and a light chain variable region (VL) at least 70% (e.g., 80%, 90%, or 95%) identical to that of mAb 7E (shown below as SEQ ID NO: 4, encoded by the nucleotide sequence of SEQ ID NO:3). See U.S. patent application Ser. No. 11/763,812.

As used herein, "percent homology" of two amino acid sequences is determined using the algorism described in Karlin and Altschul, *Proc, Natl. Acad. Sci. USA* 87:2264-2268, 1990, modified as described in Karlin and Altschul, *Proc, Natl. Acad. Sci. USA* 5873-5877, 1993. Such an algorism is incorporated into the NBLAST and XBLAST programs of Altschul et al., J. Mol. Biol. 215:403-410, 1990. BLAST protein searches are performed with the XBLAST program, score=50, wordlength=3, to obtain amino acid sequences homologous to a reference polypeptide. To obtain gapped alighments for comparison purposes, Gapped BLAST is utilized as described in Altschul et al., *Nucleic Acids Res.* 25:3389-3402, 1997. When utilizing the BLAST and Gapped BLAST programs, the default parameters of the respective programs (e.g., XBLAST and NBLAST) are used. See www.ncbi.nlm.nih.gov.

The term "treating" as used herein refers to the application or administration of a composition including one or more active agents to a subject, who has rheumatoid arthritis or osteoporosis, a symptom of either diseases, or a predisposition toward the disease, with the purpose to cure, heal, alleviate, relieve, alter, remedy, ameliorate, improve, or affect the disease, the symptoms of the disease, or the predisposition toward the disease.

"An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents As used therein, "delaying" the development of a disease (such as osteoporosis or rheumatoid arthritis) means to defer, hinder, slow, retard, stabilize, and/or postpone progression of the disease. This delay can be of varying lengths of time, depending on the history of the disease and/or individuals being treated. As is evident to one skilled in the art, a sufficient or significant delay can, in effect, encompass prevention, in that the individual does not develop the disease. A method that "delays" development of the symptom is a method that reduces probability of developing the symptom in a given time frame and/or reduces extent of the symptoms in a given time frame, when compared to not using the method. Such comparisons are typically based on clinical studies, using a number of subjects sufficient to give a statistically significant result.

"Development" or "progression" of a disease (such as osteoporosis, rheumatoid arthritis) means initial manifestations and/or ensuing progression of the disorder. Development of the disease can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of osteoporosis includes initial onset and/or recurrence.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

As used herein, "co-administration" or "administration in conjunction with" includes simultaneous administration and/or administration at different times. Co-administration also encompasses administration as a co-formulation (i.e., the IL-20 antagonist and an agent are present in the same composition) or administration as separate compositions. As used herein, co-administration is meant to encompass any circumstance wherein an agent and IL-20 antagonist are administered to an individual, which can occur simultaneously and/or separately. As further discussed herein, it is understood that the IL-20 antagonist and an agent can be administered at different dosing frequencies or intervals. For example, an anti-IL-20 antibody can be administered weekly, while the agent can be administered more frequently. It is understood that the IL-20 antagonist and the agent can be administered using the same route of administration or different routes of administration.

An "individual" or a "subject" is a mammal, more preferably a human. Mammals include, but are not limited to, farm animals, sport animals, pets, primates, horses, dogs, cats, mice and rats.

With respect to all methods described herein, reference to an IL-20 antagonist also includes compositions comprising one or more of these agents. These compositions may further comprise suitable excipients, such as pharmaceutically acceptable excipients (carriers) including buffers, which are well known in the art. The present invention can be used alone or in combination with other conventional methods of treatment.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and variations of the invention described herein include "consisting" and/or "consisting essentially of" aspects and variations.

IL-20 Antagonists

The present invention is useful for treating, delaying development of and/or preventing osteoporosis and rheumatoid arthritis in an individual in need thereof, both human and non-human mammalian.

The methods of the invention use an IL-20 antagonist, which refers to any molecule that blocks, suppresses or reduces (including significantly) IL-20 biological activity, including downstream pathways mediated by IL-20 signaling, such as receptor binding and/or elicitation of a cellular response to IL-20. An example of an IL-20 is human IL-20. The amino acid sequence of a human IL-20 (SEQ ID NO:6) is as follows:

<u>MKASSLAFSLLSAAFYLLWTPSTGLKTLNLGSCVIATNLQEIRNGFSE</u>
<u>IRGSVQAKDGNI</u>

DIRILRRTESLQDTKPANRCCLLRHLLRLYLDRVFKNYQTPDHYTLRK
ISSLANSFLTIK

KDLRLCHAHMTCHCGEEAMKKYSQILSHFEKLEPQAAVVKALGELDIL
LQWMEETE
(the signal peptide is undelined).

Exemplary IL-20 antagonists include, but are not limited to, an anti-IL-20 antibody or fragment thereof, an anti-sense molecule directed to an IL-20 (including an anti-sense molecule directed to a nucleic acid encoding IL-20), a small interfering RNA (siRNA) directed toward an IL-20 nucleic acid, a microRNA directed toward an IL-20 nucleic acid, an IL-20 inhibitory compound, and a polypeptide comprising a extracellular portion of an IL-20 receptor. For purpose of the present invention, it will be explicitly understood that the term "antagonist" encompass all the previously identified terms, titles, and functional states and characteristics whereby the IL-20 itself, an IL-20 biological activity (including but not limited to its ability to mediate any aspect osteoporosis, inflammatory diseases), or the consequences of the biological activity, are substantially nullified, decreased, or neutralized in any meaningful degree. In some embodiments, an IL-20 antagonist binds IL-20 and prevents IL-20 from forming a complex with one or more of its receptors. In other embodiments, an IL-20 antagonist inhibits or reduces IL-20 synthesis and/or production (release). Accordingly, in some embodiments, an IL-20 antagonist binds (physically interacts with) IL-20. In some embodiments, the IL-20 antagonist is a polypeptide which binds to IL-20. In some embodiments, the IL-20 antagonist is a peptide or a modified peptide (such as IL-20 binding peptide including soluble receptors of IL-20 fused to a Fc domain). See for example; U.S. Pat. Nos. 6,610,286; 7,189,394; 7,364,732; 7,393,684; and 7,537,761; and U.S. patent Application Pub. Nos. 2006/0263850 A1; 2006/0263851 A1; 2008/0171041 A1; and US 2008/0233115 A1. In other embodiments, the IL-20 antagonist is an anti-IL-20 antibody. In still other embodiments, the anti-IL-20 antibody is humanized. In some embodiments, the anti-IL-20 antibody is antibody mAb 7E (as described herein) or a functional equivalent of mAb 7E. In other embodiments, the anti-IL-20 antibody comprises one or more CDR(s) of antibody mAb 7E (such as one, two, three, four, five, or, in some embodiments, all six CDRs from mAb 7E). In other embodiments, the antibody is a human antibody. In still other embodiments, the anti-IL-20 antibody comprises the amino acid sequence of the heavy chain variable region (SEQ ID NO:2) and/or the amino acid sequence of the light chain variable region (SEQ ID NO:4). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in *Eur. J. Immunol.* (1999) 29:2613-2624; PCT Application No. PCT/GB99/01441; and/or UK Patent Application No. 9809951.8. In other embodiments, an IL-20 antagonist inhibits (reduces) IL-20 synthesis and/or release.

Nucleotide sequence (SEQ ID NO:1) and amino acid sequence (SEQ ID NO:2) of mAb 7E heavy chain variable region

```
gaa ttg aag ctt gag gag tct gga gga ggc ttg gtg cag cct gga   45
 E   L   K   L   E   E   S   G   G   G   L   V   Q   P   G    15 gga tcc atg aaa ctc tct tgt gct gcc tct gga ttc act ttt agt   90
 G   S   M   K   L   S   C   A   A   S   G   F   T   F   S    30 gac gcc tgg atg gac tgg gtc cgc cag tct cca gag aag ggg ctt  135
 D   A   W   M   D   W   V   R   Q   S   P   E   K   G   L    45 gag tgg att gct gaa att aga agc aaa gct aat aat tat gca aca  180
 E   W   I   A   E   I   R   S   K   A   N   N   Y   A   T    60 tac ttt gct gag tct gtg aaa ggg agg ttc acc atc tca aga gat  215
 Y   F   A   E   S   V   K   G   R   F   T   I   S   R   D    75 gat tcc aaa agt ggt gtc tac ctg caa atg aac aac tta aga gct  270
 D   S   K   S   G   V   Y   L   Q   M   N   N   L   R   A    90 gag gac act ggc att tat ttc tgt acc aag tta tca cta cgt tac  315
 E   D   T   G   I   Y   F   C   T   K   L   S   L   R   Y   105
```

```
                                    -continued
tgg ttc ttc gat gtc tgg ggc gca ggg acc acg gtc acc gtc tcc  360
 W   F   F   D   V   W   G   A   G   T   T   V   T   V   S   120 tca                                                          363
 S                                                           121
```

Nucleotide sequence (SEQ ID NO:3) and amino acid sequence (SEQ ID NO:4) of mAb 7E light chain variable region

```
gat ttt gtg atg acc cag act cca ctc act ttg tcg gtt acc att  45
 D   F   V   M   T   Q   T   P   L   T   L   S   V   T   I   15 gga caa cca gcc tcc atc tct tgc aag tca agt cag agc ctc ttg  90
 G   Q   P   A   S   I   S   C   K   S   S   Q   S   L   L   30 gat agt gat gga aag aca tat ttg aat tgg ttg tta cag agg cca  135
 D   S   D   G   K   T   Y   L   N   W   L   L   Q   R   P   45 ggc cag tct cca aag cac ctc atc tat ctg gtg tct aaa ctg gac  180
 G   Q   S   P   K   H   L   I   Y   L   V   S   K   L   D   60 tct gga gtc cct gac agg ttc act ggc agt gga tca ggg acc gat  215
 S   G   V   P   D   R   F   T   G   S   G   S   G   T   D   75 ttc aca ctg aga atc agc aga gtg gag gct gag gat ttg gga gtt  270
 F   T   L   R   I   S   R   V   E   A   E   D   L   G   V   90 tat tat tgc tgg caa agt aca cat ttt ccg tgg acg ttc ggt gga  315
 Y   Y   C   W   Q   S   T   H   F   P   W   T   F   G   G   105 ggc acc aag ctg gaa atc aaa cgg                              339
 G   T   K   L   E   I   K   R                               113
```

Anti-IL-20 Antibodies

In some embodiments of the invention, the IL-20 antagonist comprises an anti-IL-20 antibody. Anti-IL-20 antibodies are known in the art, see, e.g., U.S. Pat. Nos. 7,435,800; 7,115,714; 7,119,175; 7,151,166; and 7,393,684; and PCT publications WO 2007/081465; WO 99/27103; WO 2004/085475; and WO 2005052000.

In another embodiment, the anti-IL-20 antibody comprises one or more CDR(s) of antibody mAb 7E (such as one, two, three, four, five, or, in some embodiments, all six CDRs from mAb 7E). In some embodiments, the anti-IL-20 antibody comprises the three CDRs from the heavy chain and the three CDRs from the light chain of the antibody produced by the cell line having ATCC No. PTA-8687 or progeny thereof. In some embodiments, the anti-IL-20 antibody comprises the three heavy chain CDRs from the amino acid sequence shown in SEQ ID NO:2 and the three light chain CDRs from the amino acid sequence shown in SEQ ID NO:4.

Determination of CDR regions is well within the skill of the art. CDR(s) may be Kabat, Chothia, or a combination of Kabat and Chothia. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) *Nature* 342:877; Al-lazikani et al (1997) *J. Molec. Biol.* 273:927-948)). As used herein, a CDR may refer to CDRs defined by either approach or by a combination of both approaches.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). For purposes of this invention, the antibody reacts with IL-20 in a manner that inhibits IL-20 and/or downstream pathways mediated by the IL-20 signaling function. In one embodiment, the antibody is a human antibody, a humanized antibody or a chimeric antibody which recognizes one or more epitopes on human IL-20. In some embodiments, the anti-IL-20 antibody binds to the same epitope on human IL-20 as antibody mAb 7E. In other embodiments, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in *Eur. J. Immunol.* (1999) 29:2613-2624; PCT Application No. PCT/GB99/01441; and/or UK Patent Application No. 9809951.8.

The binding affinity of an anti-IL-20 antibody to IL-20 (such as human IL-20) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to IL-20 is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BIAcore, INC, Piscaway N.J.).

Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human IL-20, and does not significantly bind an IL-20 from another mammalian species. In some embodiments, the antibody binds human IL-20 as well as one or more IL-20 from another mammalian species. In still other embodiments, the antibody binds IL-20 and does not significantly cross-react with other cytokines (such as the related cytokines IL-10, IL-17A, IL-19, IL-22, IL-24 and IL-26). The epitope(s) bound by the antibody can be continuous or discontinuous. In one embodiment, the antibody binds essentially the same human IL-20 epitopes as antibody mAb 7E.

The anti-IL-20 antibodies may be made by any method known in the art. For example, antibodies that can inhibit IL-20 may be made by immunization using full length or partial sequence of IL-20 as immunogens The route and schedule of immunization of the host animal are generally in keeping with established and conventional techniques for antibody stimulation and production, as further described herein. General techniques for production of mouse, humanized and human antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) *Nature* 256:495-497 or as modified by Buck, D. W., et al., *In Vitro,* 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-IL-20 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for IL-20, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human IL-20, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, the anti-IL-20 antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to IL-20 and greater efficacy in inhibiting IL-20. It will be apparent to one of skill in the art that one or more polynucleotide changes can be made to the anti-IL-20 antibody and still maintain its binding ability to IL-20.

"Humanized" antibodies generally refer to a molecule having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody. In some instances, framework region (FR) residues or other residues of the human immunoglobulin replaced by corresponding non-human residues. Furthermore, humanized antibodies may comprise residues which are not found in the recipient antibody or in the donor antibody. Humanization can also include affinity maturation.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) *Annu. Rev. Immunol.*

12:433-455. Alternatively, the phage display technology (McCafferty et al., (1990) *Nature* 348:552-553) can be used to produce human antibodies and antibody fragments in vitro, from immunoglobulin variable (V) domain gene repertoires from unimmunized donors.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., (1984) *Proc. Nat. Acad. Sci.* 81:6851, or by covalently joining to the immunoglobulin coding sequence all or part of the coding sequence for a non-immunoglobulin polypeptide. In that manner, "chimeric" or "hybrid" antibodies are prepared that have the binding specificity of an anti-IL-20 monoclonal antibody herein.

Anti-IL-20 antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-IL-20 antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an anti-IL-20 antibody. In another example, the epitope to which the anti-IL-20 antibody binds can be determined in a systematic screening by using overlapping peptides derived from the IL-20 sequence and determining binding by the anti-IL-20 antibody. According to the gene fragment expression assays, the open reading frame encoding IL-20 is fragmented either randomly or by specific genetic constructions and the reactivity of the expressed fragments of IL-20 with the antibody to be tested is determined. The gene fragments may, for example, be produced by PCR and then transcribed and translated into protein in vitro, in the presence of radioactive amino acids. The binding of the antibody to the radioactively labeled IL-20 fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant IL-20 in which various fragments of the IL-20 polypeptide have been replaced (swapped) with sequences from a closely related, but antigenically distinct protein (such as another member of the neurotrophin protein family). By assessing binding of the antibody to the mutant IL-20, the importance of the particular IL-20 fragment to antibody binding can be assessed.

Yet another method which can be used to characterize an anti-IL-20 antibody is to use competition assays with other antibodies known to bind to the same antigen, i.e., various fragments on IL-20, to determine if the anti-IL-20 antibody binds to the same epitope as other antibodies. Competition assays are well known to those of skill in the art.

Other IL-20 Antagonists

IL-20 antagonists other than anti-IL-20 antibodies may be used. In some embodiments of the invention, the IL-20 antagonist comprises at least one antisense molecule capable of blocking or decreasing the expression of a functional IL-20. Nucleotide sequences of the IL-20 are known and are readily available from publicly available databases. See for example, Genbank accession numbers NM 018724.3 and NP 061194.2. It is routine to prepare antisense oligonucleotide molecules that will specifically bind IL-20 mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well know in the art.

Alternatively, IL-20 expression and/or release can be decreased using gene knockdown, morpholino oligonucleotides, small interfering RNA (siRNA or RNAi), microRNA or ribozymes, methods that are well-known in the art.

In other embodiments, the IL-20 antagonist comprises at least one IL-20 inhibitory compound. As used herein, "IL-20 inhibitory compound" refers to a compound other than an anti-IL-20 antibody that directly or indirectly reduces, inhibits, neutralizes, or abolishes IL-20 biological activity. An IL-20 inhibitory compound should exhibit any one or more of the following characteristics: (a) binds to IL-20 and inhibits IL-20 biological activity and/or downstream pathways mediated by IL-20 signaling function; (b) prevents, ameliorates, or treats any aspect of osteoporosis or rheumatoid arthritis; (c) blocks or decreases IL-20 receptor activation; (d) increases clearance of IL-20; (e) inhibits (reduces) IL-20 synthesis, production or release. One skilled in the art can prepare other small molecules IL-20 inhibitory compounds.

In some embodiments, an IL-20 inhibitory compound is an IL-20 mutant which can bind to an IL-20 receptor but can not elicit signal transduction. In some embodiments, the IL-20 inhibitory compound is an IL-20 mutant which blocks binding of wild type IL-20 to an IL-20 receptor thus preventing IL-20 signal transduction.

In some embodiments, IL-20 inhibitory compounds comprise small molecules, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the IL-20-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

In some embodiments, the IL-20 antagonists include a polypeptide comprising an extracellular portion of an IL-20 receptor (such as IL-20 R1, IL-20R2, or IL-22R1), wherein the polypeptide specifically binds to 11-20 and blocks its interaction with one or more IL-20 receptors. In some embodiments, the extracellular portion of the IL-20 receptor is fused to a Fc domain of antibody. Examples of the soluble receptors are described in PCT WO 01/46232.

Identification of IL-20 Antagonists

Anti-IL-20 antibodies and other IL-20 antagonists can be identified or characterized using methods known in the art, whereby reduction, amelioration, or neutralization of an IL-20 biological activity is detected and/or measured. For example, an ELISA-type assay may be suitable for qualitative or quantitative measurement of IL-20 mediated kinase activation by measuring the phosphorylation of proteins activated through an IL-20 cascade. Examples include JNK, ERK, AKT, p38, STAT3 and TRAF6.

The IL-20 antagonists can also be identified by incubating a candidate agent with IL-20 and monitoring any one or more of the following characteristics: (a) binding to IL-20 and inhibiting IL-20 biological activity and/or downstream pathways mediated by IL-20 signaling function; (b) preventing, ameliorating, or treating any aspect of osteoporosis or rheumatoid arthritis; (c) blocking or decreasing IL-20 receptor activation; (d) increasing clearance of IL-20; (e) inhibiting (reducing) IL-20 synthesis, production or release. In some embodiments, an IL-20 antagonist is identified by incubating a candidate agent with IL-20 and monitoring binding and attendant reduction or neutralization of a biological activity of IL-20. The binding assay may be performed with purified IL-20 polypeptide(s), or with cells naturally expressing, or transfected to express, IL-20 polypeptide(s). In one embodiment, the binding assay is a competitive binding assay, where the ability of a candidate antibody to compete with a known IL-20 antagonist for IL-20 binding is evaluated. The assay may be performed in various formats, including the ELISA format. In other embodiments, an IL-20 antagonist is identified by incubating a candidate agent with IL-20 and monitoring attendant inhibition of IL-20R1/IL-20R2 complex formation or IL-20R2/IL-22R1 complex formation. Following initial identification, the activity of a candidate anti-IL-20 antagonist can be further confirmed and refined by bioassays, known to test the targeted biological activities. Alternatively, bioassays can be used to screen candidates directly.

The examples provided below provide a number of assays that can be used to screen candidate IL-20 antagonists. Bioassays include but are not limited to MTT (3-(4,5-Dimethylthiazol-2-yl)-2,5-diphenyltetrazolium bromide) assays for proliferation of HUVEC cells; analysis of candidate agents on osteoclast differentiation, for example, as measured by TRAP staining; flow cytometry of determine competitive binding of IL-20 to cells in the presence of candidate IL-20 antagonists; and inhibition of IL-20-induced apoptosis in renal epithelial cells. In addition, RT-PCR or Real-time PCR which can be used to directly measure IL-20 expression or to measure expression of genes upregulated by IL-20 such as TNF-α, MCP-1, IL-1β, IL-6 and VEGF.

Compositions for Use in the Methods of the Invention

The compositions used in the methods of the invention comprise an effective amount of one or more IL-20 antagonists (such as anti-IL-20 antibody), and, in some embodiments, further comprise a pharmaceutically acceptable excipient. In some embodiments, the composition is for use in any of the methods described herein. Examples of IL-20 antagonists are described herein. It is understood that the compositions can comprise more than one IL-20 antagonist. For example, a composition can comprise more than one member of a class of IL-20 antagonist (e.g., a mixture of anti-IL-20 antibodies that recognize different epitopes of IL-20), as well as members of different classes of IL-20 antagonists (e.g., an anti-IL-20 antibody and an IL-20 inhibitory compound). Other exemplary compositions comprise more than one anti-IL-20 antibodies that recognize the same epitope(s), different species of anti-IL-20 antibodies that bind to different epitopes of IL-20, or different IL-20 inhibitory compounds.

The composition used in the present invention can further comprise pharmaceutically acceptable carriers, excipients, or stabilizers (Remington: The Science and Practice of Pharmacy 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The IL-20 antagonist and compositions thereof can also be used in conjunction with other agents that serve to enhance and/or complement the effectiveness of the agents.

Administration of an IL-20 Antagonist and Assessment of Treatment

The invention provides methods to treat, delay the onset of, or prevent osteoporosis in an individual. As discussed above, IL-20 is an osteoclastogenic cytokine that acts upstream RANKL-RANK signaling cascade in the development and activation of osteoclasts. Overexpression of IL-20 may stimulate osteoclast differentiation thereby reducing the capacity to repair bone damage associated with osteoporosis.

There are a number of factors that increase the risk of developing osteoporosis. For example, osteoporosis is associated with low estrogen levels that occur in postmenopause. Low estrogen levels may also be the result of early surgical removal of both ovaries. In addition, chemotherapy can result in early menopause as a result of the toxic effects of the chemotherapy on the ovaries. As shown in Examples, an IL-20 antagonist ameliorated the osteoporotic effects in oviarectomized mice. Thus, the IL-20 antagonists described here may be used to treat, delay the onset of, or prevent osteoporosis in a postmenopausal individual by administering an effective dose of an IL-20 antagonist.

Osteoporosis may also result from hormone ablation treatment. In both prostate cancer and breast cancer, it is common for patients to receive hormone ablation therapies; for example, androgen in the case of prostate cancer and estrogen in the case of breast cancer, which can lead to a decrease in bone mass and an increased risk of fractures. Thus, the IL-20 antagonists described here may be used to treat, delay the onset of, or prevent osteoporosis in an individual undergoing hormone ablation therapy by administering an effective dose of an IL-20 antagonist.

Chronic inflammation due to diseases including but not limited to rheumatoid arthritis and chronic liver disease can lead to bone damage. As shown in Examples, an IL-20 antagonist alleviated bone damage in a rat model of rheumatoid arthritis. Thus, the IL-20 antagonists described here may be used to treat, delay the onset of, or prevent osteoporosis in an individual with a chronic inflammatory condition by administering an effective dose of an IL-20 antagonist.

The IL-20 antagonist can be administered to an individual via any suitable route. For example, the IL-20 antagonist can be administered orally, intravenously, sublingually, subcutaneously, intraarterially, intrasynovially, intravescicular (such as via the bladder), intramuscularly, intracardiacly, intrathoracicly, intraperitoneally, intraventricularly, sublingually, by inhalation, by suppository, and transdermally. They can be administered orally, for example, in the form of tablets, troches, capsules, elixirs, suspensions, syrups, wafers, lollypops, chewing gum or the like prepared by art recognized procedures. It should be apparent to a person skilled in the art that the examples described herein are not intended to be limiting but to be illustrative of the techniques available.

Accordingly, in some embodiments, the IL-20 antagonist, such as an anti-IL-20 antibody, is administered to a individual in accordance with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, IL-20 antagonists can be aerosolized using a fluorocarbon formulation and a metered dose inhaler, or inhaled as a lyophilized and milled powder.

In one embodiment, an IL-20 antagonist is administered via site-specific or targeted local delivery techniques. Examples of site-specific or targeted local delivery techniques include various implantable depot sources of the IL-20 antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an IL-20 antagonist (such as anti-IL-20 antibody) may be used for administration. In some embodiments, an IL-20 antagonist may be administered neat. In some embodiments, the IL-20 antagonist comprises an anti-IL-20 antibody, and may be in various formulations, including formulations comprising a pharmaceutically acceptable excipient. Pharmaceutically acceptable excipients are known in the art, and are relatively inert substances that facilitate administration of a pharmacologically effective substance. For example, an excipient can give form or consistency, or act as a diluent. Suitable excipients include, but are not limited to, stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-IL-20 antibody can be administered using any suitable method, including by injection (e.g., intraperitoneally, intravenously, subcutaneously, intramuscularly, etc.). Anti-IL-20 antibodies can also be administered via inhalation, as described herein. Generally, for administration of anti-IL-20 antibodies, an initial candidate dosage can be about 2 mg/kg. For the purpose of the present invention, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to reduce osteoporosis or rheumatoid arthritis. An exemplary dosing regimen comprises administering an initial dose of about 2 mg/kg, followed by a weekly maintenance dose of about 1 mg/kg of the anti-IL-20 antibody, or followed by a maintenance dose of about 1 mg/kg every other week. However, other dosage regimens may be useful, depending on the pattern of pharmacokinetic decay that the practitioner wishes to achieve. For example, dosing from one-four time a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the IL-20 antagonist(s) used) can vary over time.

In general, when it is not an antibody, an IL-20 antagonist may (in some embodiments) be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present invention, the appropriate dosage of an IL-20 antagonist will depend on the IL-20 antagonist(s) (or compositions thereof) employed, the type and severity of the osteoporosis or rheumatoid arthritis to be treated, whether the agent is administered for preventive or therapeutic purposes, previous therapy, the patient's clinical history and response to the agent, and the discretion of the attending physician. Typically the clinician will administer an IL-20 antagonist, such as an anti-IL-20 antibody, until a dosage is reached that achieves the desired result.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of osteoporosis. Alternatively, sustained continuous release formulations of anti-IL-20 antibodies may be appropriate. Various formulations and devices for achieving sustained release are known in the art.

In one embodiment, dosages for an IL-20 antagonist may be determined empirically in individuals who have been given one or more administration(s) of IL-20 antagonist (such as an antibody). Individuals are given incremental dosages of an IL-20 antagonist, e.g., anti-IL-20 antibody. To assess efficacy of an IL-20 antagonist, an indicator of osteoporosis (such as bone mineral density) or rheumatoid arthritis (such as swelling, pain, stiffness, and tissue destruction in the joints) can be followed.

Administration of an IL-20 antagonist in accordance with the method in the present invention can be continuous or intermittent, depending, for example, upon the recipient's physiological condition, whether the purpose of the administration is therapeutic or prophylactic, and other factors known to skilled practitioners. The administration of an IL-20 antagonist (for example if the IL-20 antagonist is an anti-IL-20 antibody) may be essentially continuous over a preselected period of time or may be in a series of spaced dose, e.g., either before, during, or after developing osteoporosis or rheumatoid arthritis.

In some embodiments, more than one IL-20 antagonist, such as an antibody, may be present. The antagonist can be the same or different from each other. At least one, at least two, at least three, at least four, at least five different IL-20 antagonists can be present. Generally, those IL-20 antagonists have complementary activities that do not adversely affect each other. IL-20 antagonists can also be used in conjunction with other agents that serve to enhance and/or complement the effectiveness of the agents.

In some embodiments, the IL-20 antagonist is administered in conjunction with another agent. In some embodiments, the other agent is an agent for the treatment or amelioration of rheumatoid arthritis. Examples of anti-rheumatoid arthritis agents include a TNFα antagonist, for example, a polypeptide that binds TNF and inhibits TNF activity as reflected in TNF binding to a TNF-receptor. Examples of TNFα antagonists include etanercept (ENBREL®) and anti-TNFα antibodies such as infliximab (REMICADE®) and adalimumab (HUMIRA®). In one example, the etanercept polypeptide is a fusion protein containing human soluble TNF receptor (SEQ ID NO:5 shown below) and the Fc component of human IgG1 (i.e., Etanercept). In some embodiments, the other agent is an agent for the treatment or amelioration of osteoporosis. Examples of anti-osteoporosis agents include alendronate, ibandronate, risedronate, zoledronic acid, calcitonin, estrogen, selective estrogen receptor modulators, raloxifene, parathyroid hormone, and teriparatide.

Amino Acid Sequence of Human Soluble TNF Receptor (SEQ ID NO:5)

aqvaft pyapepgstc rlreyydqta qmccskcspg qhakvfctkt sdtvcdsced stytqlwnwv peclscgsrc ssdqvetqac treqnrictc rpgwycalsk qegcrlcapl rkcrpgfgva rpgtetsdvv ckpcapgtfs nttsstdicr phqic In some embodiments of the invention, the IL-20 antagonist; for example, mAb 7E or a derivative thereof, can be used in combination with an etanercept polypeptide, for treating rheumatoid arthritis or osteoporosis. The term "etanercept polypeptide" refers to a fusion protein containing a soluble receptor of tumor necrosis factor (TNF) and the Fc component of an immunoglobulin. In one example, the soluble TNF receptor is a human soluble TNF receptor having the amino acid sequence SEQ ID NO:5 shown below and its functional equivalent, i.e., a polypeptide having an amino acid sequence at least 85% (e.g., 90%, 95%, or 98%) identical to SEQ ID NO:5 and capable of binding to human TNF. The etanercept polypeptide can be made by conventional recombinant technology.

Therapeutic formulations of the IL-20 antagonist (such as an antibody) used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the IL-20 antagonist (such as an antibody) are prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic anti-IL-20 antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing an IL-20 antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol.* (1993) 11:202; Chiou et al., Gene Therapeutics: Methods And Applications Of Direct Gene Transfer (J. A. Wolff, ed.) (1994); Wu et al., *J. Biol. Chem.* (1988) 263:621; Wu et al., *J. Biol. Chem.* (1994) 269: 542; Zenke et al., *Proc. Natl. Acad. Sci. USA* (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol*. (1994) 14:2411, and in Woffendin, *Proc. Natl. Acad. Sci*. (1994) 91:1581.

It is also apparent that an expression vector can be used to direct expression of any of the protein-based IL-20 antagonists described herein (e.g., anti-IL-20 antibody, immunoadhesin, etc.). For example, other IL-20 receptor fragments that are capable of blocking (from partial to complete blocking) IL-20 and/or an IL-20 biological activity are known in the art.

Kits

The invention also provides kits for use in the instant methods. Kits of the invention include one or more containers comprising an IL-20 antagonist (such as an antibody, such as antibody mAb 7E described herein or its derivatives), and in some embodiments, further comprise instructions for use in accordance with any of the methods of the invention described herein. In some embodiments, the IL-20 antagonist is any IL-20 antagonist described herein. In other embodiments, the kit comprises an IL-20 antagonist that is other than an anti-IL-20 antibody. In some embodiment, the kit comprises an anti-IL-20 antibody (such as antibody mAb 7E described herein). In other embodiments, the kit comprises an anti-IL-20 antibody comprising one or more CDR(s) of antibody mAb 7E (such as one, two, three, four, five, or, in some embodiments, all six CDRs from mAb 7E). In some embodiments, the included instructions comprise a description of administration of the IL-20 antagonist to treat, delay the onset or prevent osteoporosis or rheumatoid arthritis according to any of the methods described herein. The kit may further comprise a description of selecting an individual suitable for treatment based on identifying whether that individual has osteoporosis or rheumatoid arthritis. In still other embodiments, the instructions comprise a description of administering an IL-20 antagonist to an individual at risk of osteoporosis or rheumatoid arthritis.

The instructions relating to the use of an IL-20 antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or preventing osteoporosis. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IL-20 antagonist, such as an anti-IL-20 antibody. The container may further comprise a second pharmaceutically active agent, such as a TNFα antagonist or another drug for treating osteoporosis.

Kits may optionally provide additional components such as buffers and interpretive information. Normally, the kit comprises a container and a label or package insert(s) on or associated with the container.

In some embodiments, the invention provides articles of manufacture comprising contents of the kits described above. In some embodiments, the kits comprise an IL-20 antagonist (such as anti-IL-20 antibody) with information indicating use to treat osteoporosis or rheumatoid arthritis.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications, references, patents and patent applications cited herein are incorporated by reference in their entirety.

EXAMPLES

Example 1

Treating Rheumatoid Arthritis with Monoclonal Antibody 7E (mAb 7E)

Rats having collagen-induced arthritis (CIA) is a well-developed animal model for studying human rheumatoid arthritis. This model was employed in this study to examine the efficacy of mAb 7E for treating this disease.

CIA was induced in eight-week-old male Sprague-Dawley rats as follows. The rats were immunized initially by intradermal injection (in the dorsum) of 200 µl emulsion containing Freund's complete adjuvant, 4 mg/ml heat-killed *Mycobacterium tuberculosis* (Arthrogen-CIA; Chondrex, Redmond, Wash.), and bovine type II collagen (CII; 2 mg/ml dissolved in 0.05 M acetic acid) at a ratio of 1:1:1 (v/v/v). Eight days later, the rats were then injected subcutaneously with 100 μl of the just-described emulsion in the roots of the tails to boost their immune responses. CIA was observed in these rats between day 11 and day 13 after the initial immunization.

The following four groups of rats (n=5) were subjected to this study: Group (1): healthy rats; Group (2): CIA rats, as described above, administered with PBS (s.c.) one week after CIA onset; Group (3): CIA rats administered with mAb 7E (3 mg/kg, s.c.) one week after CIA onset, and; Group (4): Etanercept (Enebrel®; Wyeth, USA, 3 mg/kg, s.c.) one week after CIA onset. Hind-paw thickness of each treated rat was measured with a caliper. All raw results obtained from this study were subjected to statistical analysis using statistical software Prism 4.0; GraphPad Software, San Diego, Calif., USA. The Kruskal-Wallis test was used to compare the thickness of the hind paws. P-values <0.05 were considered significant. Significant differences were evaluated using Student's t-test or one-way analysis of variance (ANOVA). Statistical significance was set at P<0.05.

As shown in Table 1 below, mAb 7E significantly reduced hind-paw thickness in CIA rats (p<0.05) and its efficacy was close to that of Etanercept, a commercially available anti-rheumatoid arthritis drug (see Mihara et al., *Br J Pharmacol.*, 2008, 154:153-164). This result indicates that, like Etanercept, mAb 7E is also effective in treating rheumatoid arthritis.

TABLE 1

Hind-Paw Thickness of Control and Treated Rats

| GROUP | Median Hind-Paw Thickness | 25th-75th Percentiles |
|---|---|---|
| 1 (health control) | 0.53 cm | 0.52-0.54 cm |
| 2 (PBS-treated) | 1.05 cm | 1.02-1.13 cm |
| 3 (mAb 7E-treated) | 0.84 cm | 0.72-0.93 cm |
| 4 (Etanercept-treated) | 0.86 cm | 0.78-0.91 cm |

Next, the effect of mAb 7E in reducing levels of inflammatory mediators in synovial tissue was examined as follows. The synovial tissues surrounding the knee joints in the treated CIA rats were isolated and suspended in a PBS solution. The tissues were then homogenized, centrifuged at 3000 rpm for 10 min at 4° C., and the supernatants thus obtained were stored at 80° C., ready for analysis. The levels of TNF-α, IL-1β (TNF-α and IL-1β kits; R&D Systems, Minneapolis, Minn.), and IL-20 (IL-20 kit; PeproTech Asia/CytoLab, Rehovot, Israel) were evaluated using a sandwich ELISA assay according to the manufacturer's instructions. It is known in the art that the levels of all these inflammatory mediators are elevated in CIA rats.

Results thus obtained indicate that mAb 7E and Etanercept significantly reduced the levels of TNF-α, IL-1β, and IL-20 as compared with mIgG. More specifically, while in mIgG-treated CIA rats, the levels of TNF-α, IL-1β, and IL-20 in synovial tissues were much higher than those in the synovial tissues of healthy control rats, they were significantly reduced in CIA rats treated with mAb 7E or Etanercept.

Example 2

Treating Rheumatoid Arthritis with Both mAb 7E and Etanercept

CIA was induced in rats following the method described in Example 1. The CIA rats were randomly assigned to five groups (n=9 in each group) and treated as follows three times per week after CIA onset: Group 1: PBS; Group 2: mouse IgG, obtained from Chemicon International, Inc., Temecula, Calif., USA; Group 3: Etanercept (6 mg/kg, s.c.); Group 4: mAb 7E (6 mg/kg, s.c.); and Group 5: mAb 7E (3 mg/kg, s.c.) and Etanercept (3 mg/kg, s.c.). First, the thickness of hind-paw of each treated rats was examined following the methods described in Example 1 above. The combined treatment of mAb 7E and Etanercept showed significantly higher effect in reducing hind-paw thickness as compared to the individual treatment of mAb 7E and Etanercept.

Next, the severity of CIA in each hind paw of the rats was monitored and scored, following the method described in Hsu et al., (*Arthritis Rheum.* 2006, 54:2722-2733). Generally, if a rat has a severity score higher than 3, that rat is considered as having severe swelling in its hind paw. The Kruskal-Wallis test was applied to compare the severity scores obtained from different groups to assess whether the results were statistical significant. As shown in Table 2 below, the median severity score of rats treated with both mAb 7E and Etanercept was much lower than that of rats treated with mAb 7E alone or with Etanercept alone. These results were statistically significant (P<0.05).

TABLE 2

Severity Score of Healthy and CIA Rats Treated with Various Agents

| GROUP | Median Severity Score | $25^{th}$ 75th Percentiles |
|---|---|---|
| Healthy controls | 0.2 | 0.0-0.4 |
| Group 1 (PBS) | 4.2 | 3.9-4.5 |
| Group 2 (mIgG) | 4.0 | 3.5-4.2 |
| Group 3 (mAb 7E) | 2.0 | 0.5-3.1 |
| Group 4 (Etanercept) | 2.1 | 0.7-3.6 |
| Group 5 (mAb 7E + Etanercept) | 0.9 | 0.0-2.2 |

The presence of severe hind-paw swelling was then examined in each treated CIA rat and the results were shown in FIG. 1. Unexpectedly, while the incidences of severe swelling in the CIA rats treated with mAb 7E and Etanercept, individually, were reduced from 100% to 22% and from 100% to 33%, respectively, the incidence of severe swelling in the CIA rats treated with both mAb 7E and Etanercept reduced from 100% to only 6%. These results, which were statistically significant as analyzed using Fisher's exact test, indicate that the combined treatment of mAb 7E and Etanercept is much more efficient than the individual treatment of mAb 7E or Etanercept.

In addition, the severity of bone damage in the treated CIA rats was examined twenty-five days after the initial immunization with bovine collagen via radio imaging. Severe bone damage was observed in hind-paw joints in the CIA rats treated with PBS and mIgG (i.e., the rats of group 1 and group 2). Surprisingly, the severity of local ankle bone damage was relatively mild in the CIA rats treated with mAb 7E, Etanercept, or the combination thereof (rats of groups 3-5). The differences between groups 1 and 2 rats and groups 3-5 rats were statistically significant (P<0.01-0.05). These results further confirm that mAb 7E alleviated bone damage in CIA rats as efficiently as Etanercept and the combined treatment of mAb 7E and Etanercept was much more efficient than the corresponding individual treatment.

Further, a microcomputed tomographic analysis, using a 1076 microCT-40 system (Skyscan, Aartselaar, Belgium) equipped with a high resolution, low-dose X-ray scanner, was performed to assess the efficacy of mAb 7E alone and its combination with Etanercept in protecting bone destruction in CIA rats. The X-ray tube in the scanner was operated with photon energy of 48 kV, current of 200 uA, and exposure time of 1180 ms through a 0.5-mm-thick filter. The image pixel size was 17.20 um, and the scanning time was approximately 15 min. After standardized reconstruction of the scanned images, the data sets for each tibia sample were resampled with software (CTAn; Skyscan) to orient each sample in the same manner. Consistent conditions such as thresholds were applied throughout all analyses. Bone mineral density, a three-dimensional bone characteristic parameter, was analyzed in 50 consecutive slices. The results were calculated as a percentage versus values relative to an mIgG control.

The tibias obtained from the CIA rats treated with PBS and mIgG showed prominent bone damage compared to the intact joints found in healthy controls. The CIA rats treated with mAb 7E displayed alleviated bone loss compared to the rats treated with mIgG. In the rats treated with both mAb 7E and Etanercept, the bone loss was even less severe relative to the rats treated with either mAb or Etanercept alone.

The bone mineral density, a quantitative parameter for assessing disease severity, was measured in each treated CIA rat as described above. mAb 7E treatment in CIA rats significantly inhibited bone loss as compared to the mIgG-treated CIA rats ($P<0.05$). The protective effects were drastically increased in the CIA rats treated with both mAb 7E and Etanercept ($P<0.01$). The microCT result supported the radiological data from their ankle joints. These results provided evidence that mAb 7E not only reduced the severity of arthritis but also inhibited bone loss.

Figure 2A:
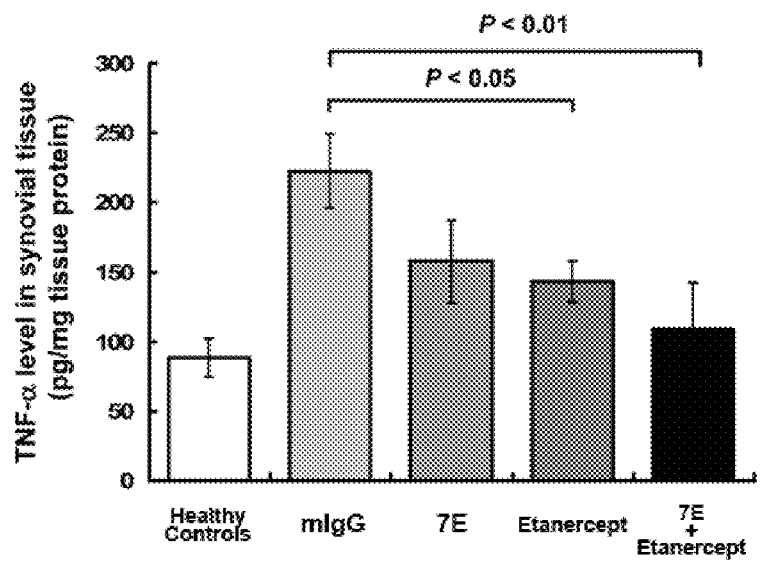
FIG. 2 is a number of charts showing the levels of TNF-α (panel A), IL-1β (panel B) and IL-20 (panel C) in healthy rats and in collagen-induced-arthritic rats treated with mIgG, mAb 7E, Etanercept, or both mAb 7E and Etanercept.
Figure 2B:
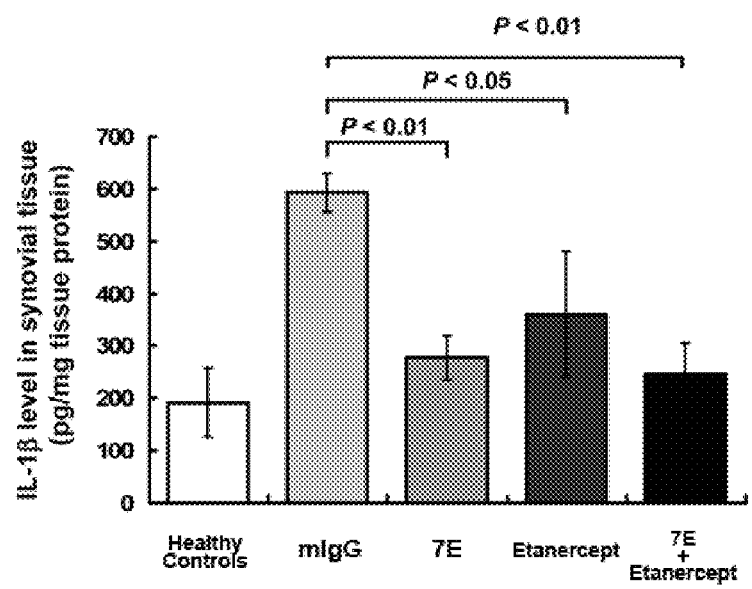
Figure 2C:
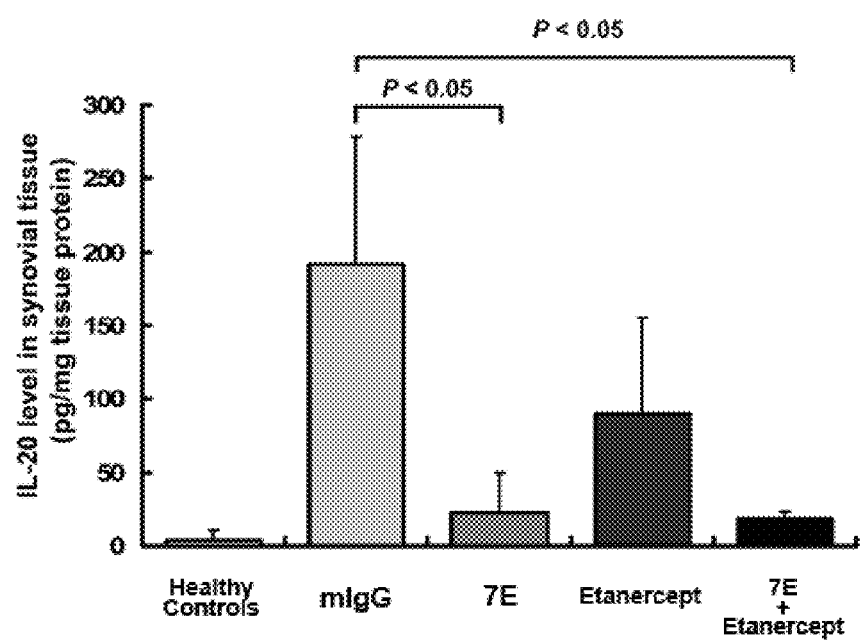

Finally, the expression levels of TNF-α, IL-1β, and IL-20 were examined in the CIA rats treated with both mAb 7E and Etanercept and the results thus obtained showed that these cytokines were significantly decreased. See FIG. 2. Expression of IL-6 was also decreased following treatment with mAb 7E, Etanercept, and mAb 7E and Etanercept together.

In sum, the results described above demonstrate that mAb 7E is effective in treating CIA by both reducing severity of arthritis and inhibiting bone loss. These results also indicate that the combined effect of mAb 7E and Etanercept is significantly higher than the individual effect of either mAb 7E or Etanercept.

Example 3

Treating Osteoporosis with mAb 7E

Fourteen-week-old female BALB/C mice (Laboratory Animal Center, National Cheng Kung University, Tainan, Taiwan) were housed in an environmentally controlled laboratory upon arrival and acclimatized for 4 days. Animals were allocated in polycarbonate cages (3 per cage) in a temperature/humidity controlled room (20-25° C. and 40-45%). The Light:dark cycle was 12-h light:12-h dark, and feed and water were supplied free to access. The animals were either dorsal ovariectomized (OVX) or falsely operated (Sham controls) under general anesthesia by using pentobarbital (50 mg/kg body weight; Sigma-Aldrich, St. Louis, Mo.). In Sham controls, bilateral ovaries were exposed and then closed with skin suture not removed. The mice were recovered for a week after OVX or control surgery and then randomly assigned to six groups: Group 1: Sham controls (n=5); Group 2: OVX mice with no further treatment (n=5); Group 3: OVX mice treated with 17β-estradiol (Sigma-Aldrich, St. Louis, Mo., 10 μg/kg/day, n=6); Group 4: OVX mice treated with mIgG (Chemicon International, Inc., Temecula, Calif., USA, 3 mg/kg/three days, n=7)); Group 5: OVX mice treated with mAb 7E (3 mg/kg/three days, n=5); and Group 6: OVX mice treated with mAb 7E (6 mg/kg/three days, n=5). The dosage of 17β-estradiol treatment used as a positive control are based on previous protocols known to be effective in treating OVX mice. See Cano et al., *Osteoporos Int.* 2008 June; 19(6):793-800.

The mice of all groups were sacrificed 2 months later. The tibia of each mouse was aseptically collected, cleaned to remove adherent soft tissues, and deposited in a tube filled with 3.7% formalin. It was then subjected to Microcomputed tomography and bone mineral density analysis following the methods described in Example 2 above.

Figure 3A:
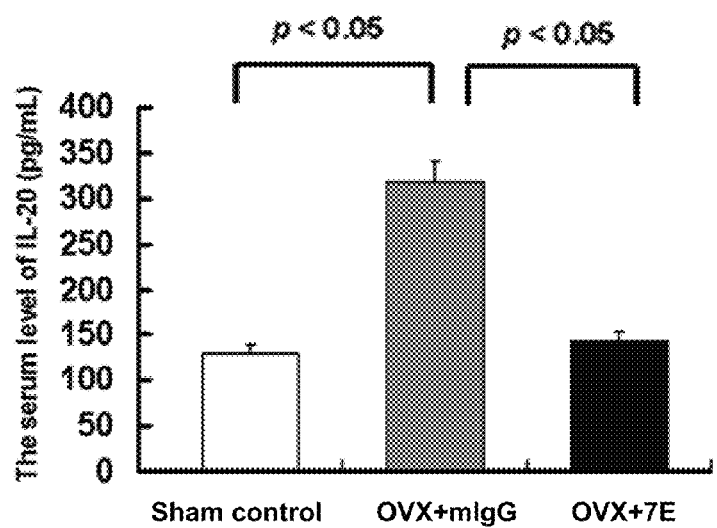
FIG. 3a is a chart showing the serum level of IL-20 was upregulated in the OVX-group mice but downregulated in OVX-mice after treatment with mAb 7E. *P<0.05 compared to sham control. #P<0.05 compared with the OVX-mIgG group.
Figure 3B:
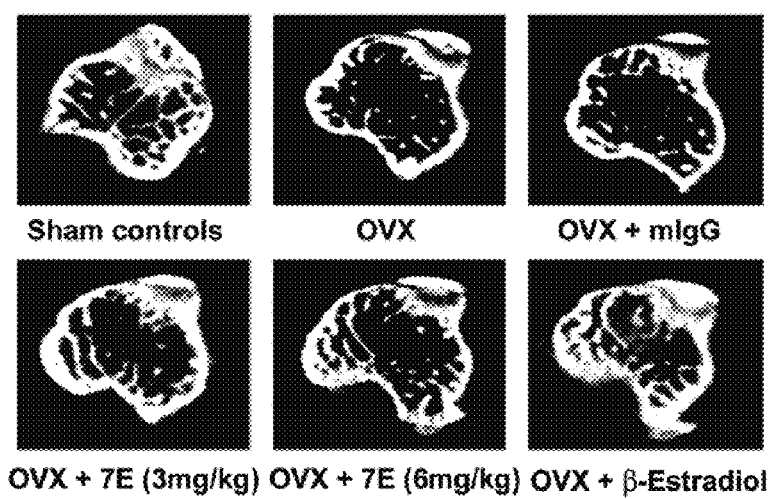
FIG. 3b shows representative figures of micro-CT analysis of the right tibia of mice 2 months after OVX with treatments: sham controls (Healthy), ovariectomized without treatment (OVX), and ovariectomized mice treated with 17β-estradiol, OVX+mIgG, OVX+7E (3 mg/kg), or OVX+7E (6 mg/kg).
Figure 3C:
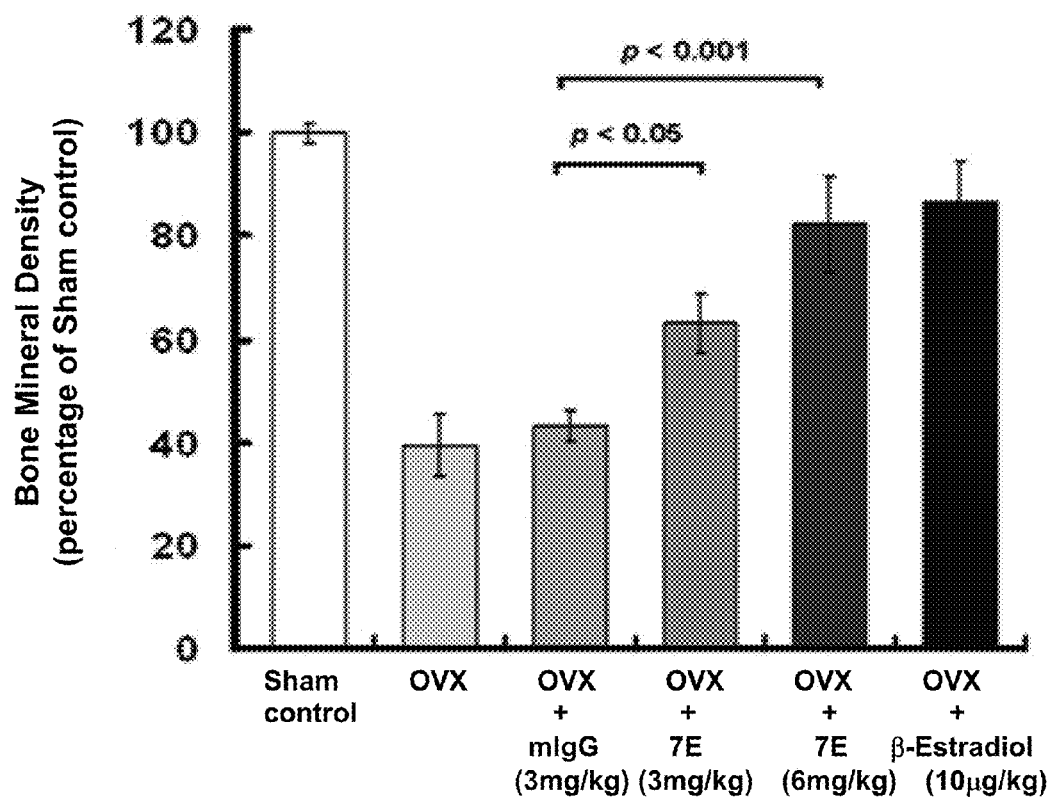
FIG. 3c is a chart showing bone mineral density in the knee joints of each experimental group. Values are means±standard deviation.

The serum level of IL-20 was upregulated in the OVX-group mice but down-regulated in OVX-mice treated with mAb 7E (FIG. 3a). MicroCT scanning of the bone mineral density of the mice tibia showed levels of bone damage in Groups 2 and 3 (untreated or treated with mIgG) were much greater than those in Groups 4-6 (treated with 3 mg/kg mAb 7E, 6 mg/kg mAb 7E, and 17β-estradiol), indicating that, like 17β-estradiol, mAb 7E also reduced bone loss in OVX mice (FIG. 3b). Further, the bone mineral densities in mAb 7E-treated and 17β-estradiol-treated OVX mice were much higher than those in Sham controls and in mIgG-treated mice (FIG. 3b). A statistically significant ($P<0.05$ compared with the mIgG controls) dose-response increase in bone density was observed in those mice (FIG. 3c). Taken together, these results demonstrate that mAb 7E is effective in treating osteoporosis by reducing bone loss.

Example 4

IL-20 Antibody mAb 7E Inhibits Osteoclast Differentiation

Bone formation is tightly regulated by crosstalk between osteoblasts and osteoclasts. Unbalanced osteoclastogenesis causes bone loss in osteoporosis and rheumatoid arthritis (Takayanagi, H, et al. (2005) *Immunol Rev* 208:181-193; Ross, F P and Teitelbaum, S L (2005) *Immunol Rev* 208:88-105). Thus, we wanted to determine whether mAb 7E protects against bone loss in OVX mice by inhibiting the differentiation of osteoclasts.

Bone marrow cells (BMCs) were prepared from the tibias of mice and incubated for 12 h (37° C./5% $CO_2$). Later, non-adherent cells were collected and seeded in 24-well plates ($2\times10^6$ cells per well) and cultured in the same medium supplemented with 30 ng/ml recombinant murine macrophage colony stimulating factor (M-CSF) (PreproTech). After 48 h, M-CSF-derived BMCs were cultured with murine M-CSF (40 ng/ml) and sRANKL (100 ng/ml) (PreproTech) until the end of experiment. To test the effect of mAb 7E, MCSF-derived BMCs were treated with IL-20 (200 ng/ml), mAb 7E (2 μg/ml), mIgG (2 μg/ml) in α-MEM with M-CSF and sRANKL until the end of the experiment.

For earlier treatment with mAb 7E, the BMCs were cultured for 12 h. Non-adherent cells were seeded in 24-well plates ($2\times10^6$ cells per well) and cultured in α-MEM containing mAb 7E (2 μg/ml) or control mIgG (2 μg/ml), after which M-CSF (40 ng/ml) was added. After 40 h, the mAb 7E treatment was ended, the cells were washed with serum-free culture medium and then incubated until the end of the experiments in α-MEM (40 ng/ml) and sRANKL (100 ng/ml). To calculate the number of osteoclasts, the cells were fixed in acetone and stained for TRAP using an acid phosphatase kit (Sigma-Aldrich).

Figure 4A:
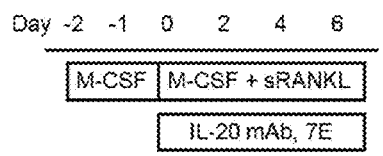
FIG. 4a is a schematic of the culture system for osteoclast differentiation.
Figure 4B:
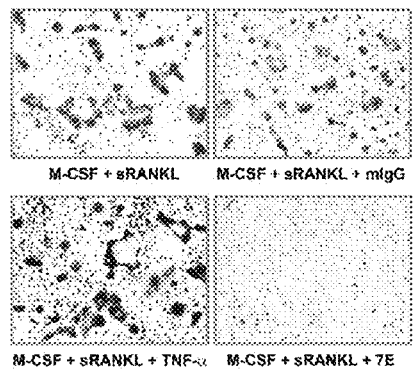
FIG. 4b shows representative tartrate-resistant acid phosphatase (TRAP) staining of osteoclasts for the treatments of macrophage colony-stimulating factor (M-CSF) and soluble NF-κB ligand receptor activator (sRANKL) combined with tumor necrosis factor (TNF)-α, mIgG, or mAb 7E.
Figure 4C:
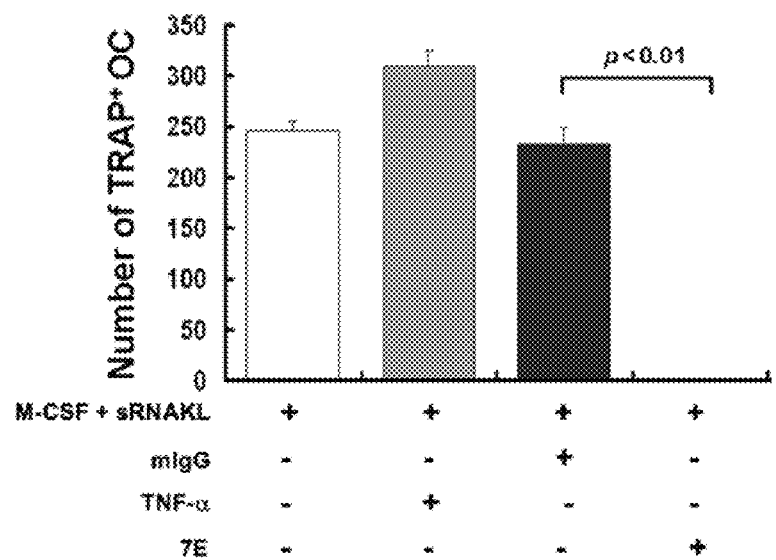
FIG. 4c is a chart showing the number of TRAP+ osteoclasts per well.
Figure 4D:
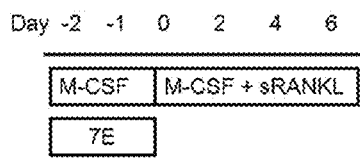
FIG. 4d is a schematic of the osteoclast differentiation culture system for early mAb 7E treatment.
Figure 4E:
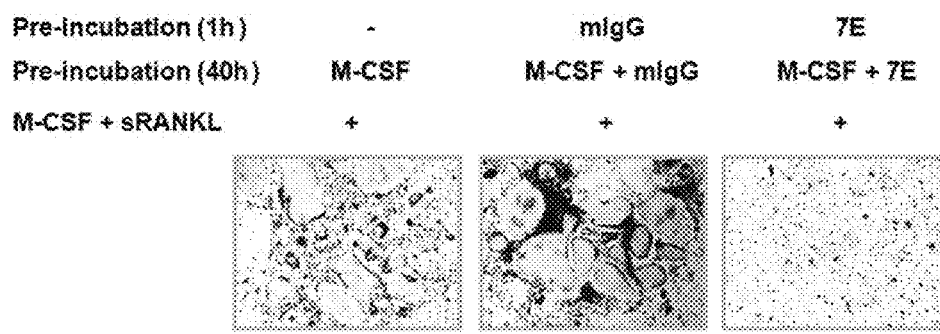
FIG. 4e shows TRAP staining of osteoclasts.
Figure 4F:
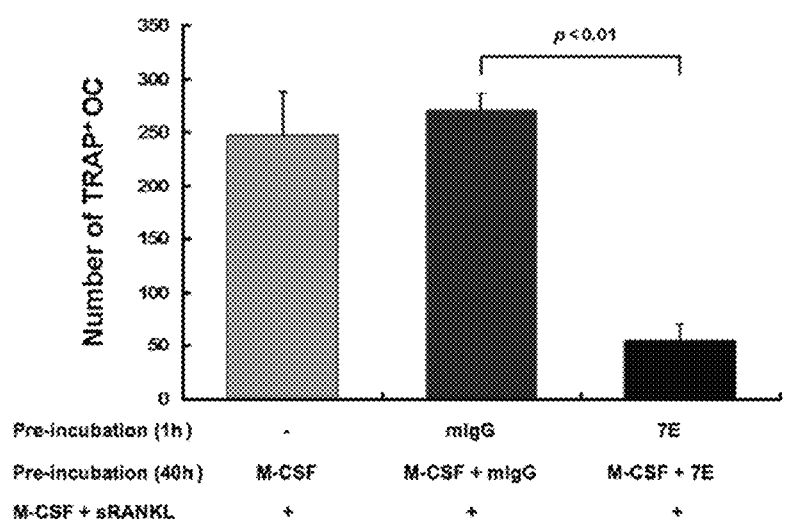
FIG. 4f is a chart showing the number of TRAP+osteoclasts per well. Representative results from 3 independent experiments are shown.

Osteoclast precursor cells were prepared from bone marrow-derived hematopoietic stem cells (HSCs), and both M-CSF and soluble (s) RANKL were added to the culture to drive OC differentiation. Two culture protocols were used to analyze the effect of IL-20 antibody mAb 7E on OC differentiation in the early and later stages of osteoclastogenesis (FIG. 4). After 48 h, M-CSF-derived bone marrow macrophages were cultured with murine M-CSF (40 ng/ml) and sRANKL (100 ng/ml) until the end of experiment. TRAP staining was used to quantify the number of differentiated osteoclasts. In the presence of mAb 7E (2 µg/ml), the number of TRAP+ osteoclasts was significantly (P<0.01) lower than in the isotype controls (FIGS. 4b and 4c). No OC was detected in the presence of mAb 7E. To clarify whether the mAb 7E affected OC differentiation in early or later stages, bone marrow cells were pre-incubated with mAb 7E or mIgG for 1 h and then M-CSF was added for another 48 h. The cells were collected and cultured for 3 more days in medium containing M-CSF and sRANKL without mAb 7E antibody (FIG. 4d). Early incubation with mAb 7E efficiently inhibited osteoclast differentiation (P<0.01 compared with the mIgG controls) (FIGS. 4e and 4f). Thus, IL-20 antibody blocked both the early and later stages of osteoclast differentiation.

Additionally, IL-20 induced TNFα and RANKL expression in synovial fibroblasts from the CIA rat model of rheumatoid arthritis but not in synovial fibroblasts from healthy rats.

Example 5

M-CSF Upregulated IL-20 in HSCs

Figure 5A:
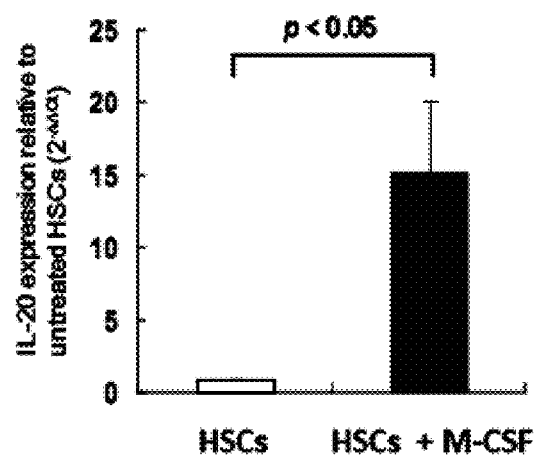
FIG. 5a is a chart showing IL-20 expression in bone marrow-derived hematopoietic stem cells (HSCs) with or without MCSF.

IL-20 antibody mAb 7E blocked the differentiation of osteoclasts from bone marrow-derived HSCs (FIG. 4). To test this possibility that HSCs secreted IL-20 into culture medium, IL-20 expression in the bone marrow-derived HSCs that had been cultured and treated with M-CSF for 48 h was examined. Real-time PCR(RT-PCR) showed that IL-20 mRNA was higher in HSCs treated with M-CSF than in controls (FIG. 5a), evidence that IL-20 had been endogenously secreted in response to M-CSF stimulation. For RT-PCR, SYBR Green I (Bio-Rad) chemistry using a fluorescence detection system (DNA Engine Opticon 2; Bio-Rad). The fluorescence- and time-dependent generation of signals was assessed using the manufacturer's software.

IL-20 receptors were also expressed in the M-CSF-derived OC precursor cells. These results suggested that IL-20 acted on the HSC-derived osteoclast precursor cells in an autocrine manner.

Example 6

Figure 5B:
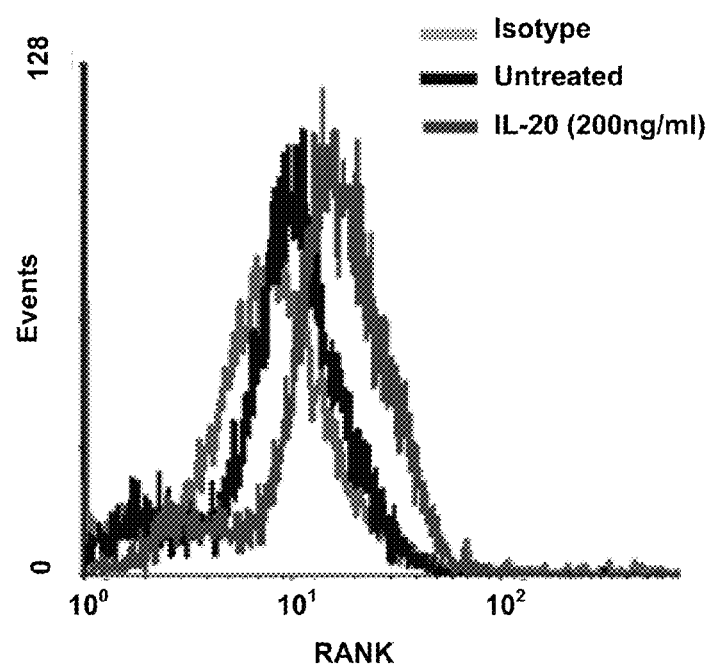
FIG. 5b shows flow cytometric analysis of the surface expression of RANK protein IL-20-treated HSCs. Isotype indicates cells stained with a negative control of isotype antibody.
Figure 5C:
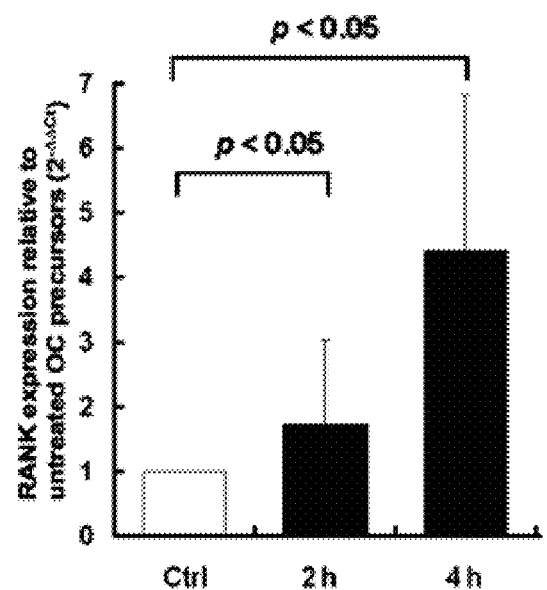
FIG. 5c is a chart showing that RANK mRNA expression was upregulated in HSCs after they had been treated with IL-20.

IL-20-induced RANK Expression in M-CSF-derived OC Precursors from Bone Marrow Cells The RANKL-RANK signal is critical for osteoclast differentiation (Wada, T et al. (2006) *Trends Mol Med* 12:17-25). RANK is expressed on the surface of osteoclasts. To investigate whether IL-20 increased osteoclast differentiation by increasing RANKL-RANK signaling, RANK expression was analyzed in M-CSF-derived osteoclast precursors from bone marrow cells. The cells were harvested by scraping, incubated for 30 min with 0.5 mg/ml anti-murine RANK antibody (eBioscience) or isotype control antibody, incubated with fluoroisothiocyanate (FITC)-conjugated secondary antibody, and then analyzed using a flow cytometer (FACSCalibur; BD Biosciences), with 20000 events acquired for each sample. Flow cytometric analysis showed that, in IL-20-treated M-CSF-derived OC precursors, the surface expression of RANK protein (FIG. 5b) and of RANK mRNA (FIG. 5c) was upregulated in osteoclast precursors.

Figure 5D:
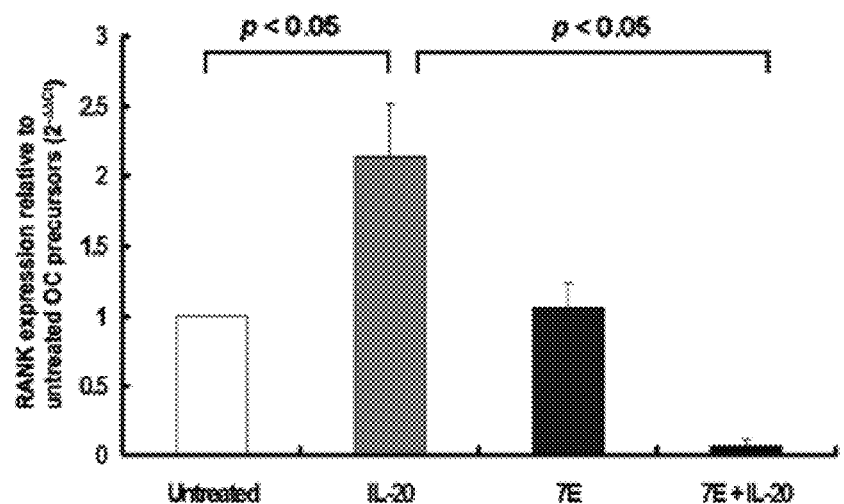
FIG. 5d is a chart showing that mAb 7E inhibited IL-20-induced RANK mRNA expression in OC precursor cells as measured by real time-PCR.

Consistent with the inhibitory effect of mAb 7E on osteoclast differentiation, mAb 7E treatment inhibited both the expression of RANK transcripts (FIG. 5d) and the surface expression of RANK protein. M-CSF-derived BMCs were cultured for 24 h with the indicated concentrations of IL-20, mIgG, mAb 7E, or both IL-20 and mAb 7E in α-MEM containing M-CSF (50 ng/ml) and sRANKL (100 ng/ml). To assay RANK production, the cells were stimulated with IL-20 (200 ng/ml), trypsinized, and then stained with PE-conjugated antibody against RANK (eBioscience) for flow cytometric analysis as described above. These results are evidence that IL-20 acts on osteoclast precursors as an osteoclastogenic cytokine by increasing their RANK expression.

Example 7

IL-20 Targeted Osteoblasts and Upregulated RANKL Expression

Figure 6A:
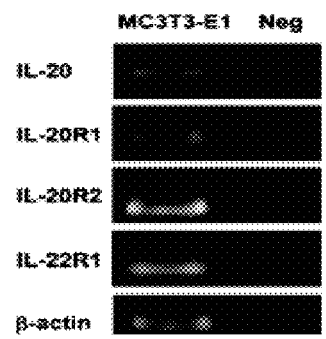
FIG. 6a shows the expression of IL-20 and its receptors in MC3T3-E1 osteoblasts by RT-PCR.
Figure 6B:
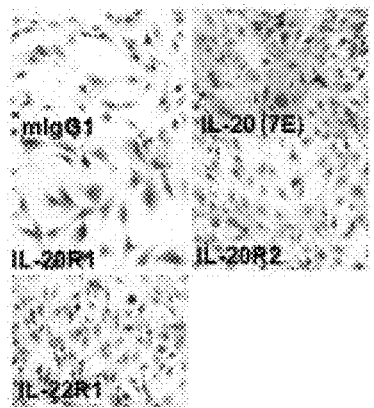
FIG. 6b shows cell staining of IL-20 and its receptors in MC3T3-E1 cells: red (IL-20 and receptors, AEC), blue (nuclei).
Figure 6C:
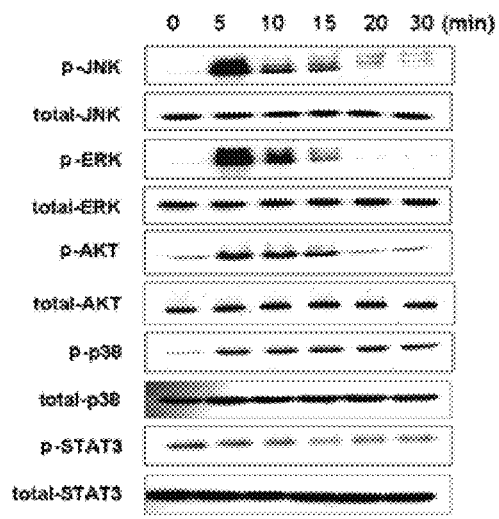
FIG. 6c shows western blot analysis of cells incubated with IL-20 for the indicated time periods using the following specific antibodies: phospho-JNK (JNK), phospho-ERK (ERK), phospho-AKT (AKT), phospho-p38 (p38), phospho-STAT3 (STAT3), and β-actin (β-actin).
Figure 6D:
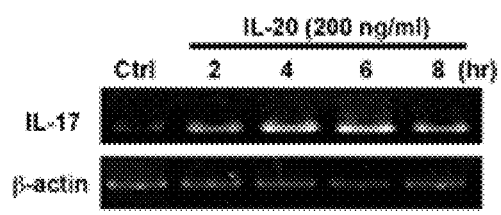
FIG. 6d shows RT-PCR analysis of IL-17 mRNA expression in MC3T3-E1 cells treated with IL-20.
Figure 6E:
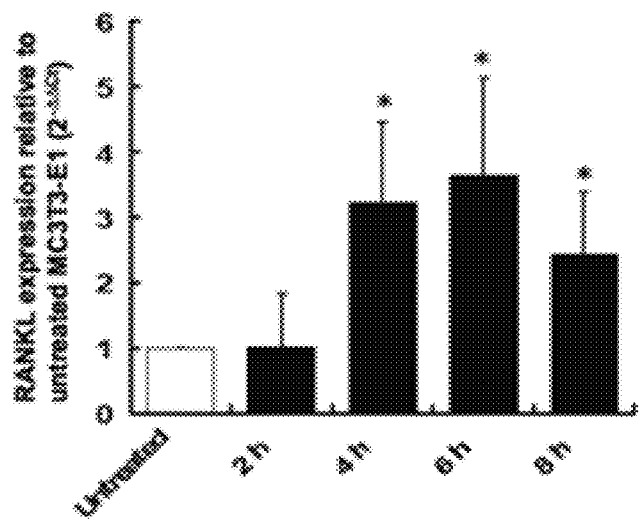
FIG. 6e is a chart showing RANKL mRNA expression in MC3T3-E1 cells treated with IL-20 and measured by Real time-PCR.
Figure 6F:
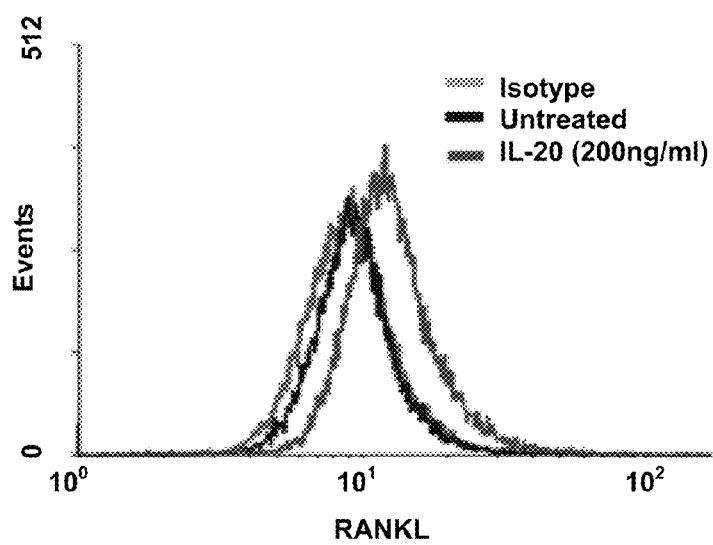
FIG. 6f is a chart showing RANKL protein expression in MC3T3-E1 cells treated with IL-20.

Increased RANKL expression in osteoblasts is also a key factor for osteoclastogenesis (Jordan, W J et al. (2005) *Eur J Immunol* 35:1576-1582). RT-PCR analysis (FIG. 6a) and cytochemical staining (FIG. 6b) were used to clarify the function of IL-20 in osteoblasts. Both in vitro assays showed that IL-20 and its three receptor subunits were expressed in MC3T3-E1 osteoblasts. To assess the phosphorylation pattern of several signal transduction proteins, MC3T3-E1 cells were stimulated with murine IL-20 (200 ng/ml) (R&D Systems, Minneapolis, Minn., USA) for the indicated times. Western blotting was done with antibodies specific for phosphorylated ERK, AKT, STAT3, p38, and JNK (Cell Signaling Technology) using the manufacturer's instructions. As shown in FIG. 4c, JNK, ERK, AKT, and p38 were phosphorylated in IL-20-treated MC3T3-E1 osteoblasts thus providing more evidence that IL-20 was endogenously expressed in osteoblasts and triggered signal transduction in them in an autocrine manner. It was recently reported that Th17 is critical in the induction and progression of RA. Th17 involvement in RA pathogenesis has been attributed to IL-17-stimulated osteoclastogenesis (Kotake, S, et al. (1999) *J. Clin. Invest.* 103:1345-1352). Transcripts of IL-17 were higher in IL-20-treated MC3T3-E1 osteoblasts (FIG. 6d). To determine whether IL-20 contributes to osteoclastogenesis by inducing RANKL expression in osteoblasts, MC3T3-E1 cells with IL-20 and analyzed RANKL expression using real-time-PCR and flow cytometry. RANKL expression was time-dependently higher in IL-20-treated cells than in untreated controls, and peaked 6 h after treatment (FIG. 6e). The surface expression of RANKL protein was also higher in IL-20-treated MC3T3-E1 cells (FIG. 6f). IL-20 acted on Th17 cells and induced the release of RANKL. Moreover, IL-20 and IL-17 synergistically induce more RANKL expression, which in turn, increases osteoclast differentiation and leads to bone erosion.

Example 8

IL-20 Antibody Inhibited IL-20-induced RANKL Expression in Osteoblasts

Figure 7:
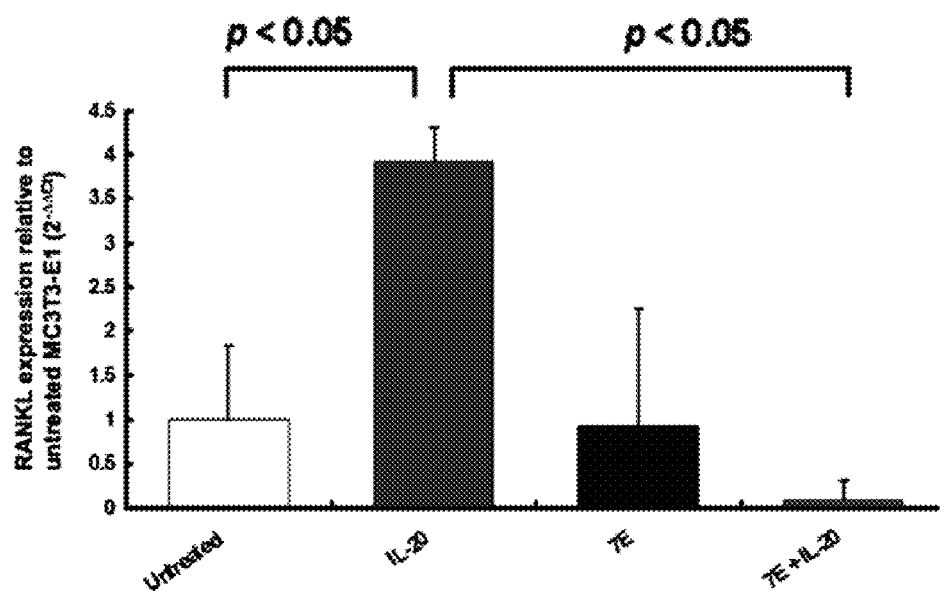
FIG. 7 is a chart showing mAb 7E inhibited IL-20-induced RANKL expression in MC3T3-E1 osteoblasts. Representative results from 3 independent experiments are shown.

As discussed above, RANKL expression was higher in IL-20-treated than in untreated MC3T3-E1 cells (FIGS. 6e and 6f). To confirm that IL-20 antibody mAb 7E inhibits IL-20-induced RANKL expression, cells were co-treated with IL-20 and mAb 7E. Real-time-PCR showed that no RANKL transcripts were detected in co-treated cells (FIG. 7). These results indicated that IL-20 is an upstream activator for RANKL expression in osteoblasts, and that mAb 7E inhibits IL-20-induced RANKL expression. The results provided strong evidence that IL-20 is, in vitro, an upstream inducer of RANKL in osteoblasts, and that this promotes osteoclastogenesis.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Although the foregoing invention has been described in some detail by way of illustration and example for purposes of clarity of understanding, the descriptions and examples should not be construed as limiting the scope of the invention.

---

What is claimed is:

1. A method for treating osteoporosis in an individual comprising administering to the individual an effective amount of an antibody that specifically binds to IL-20 or an antigen binding fragment thereof.

2. The method of claim 1, wherein the antibody or antigen binding fragment specifically binds to human IL-20 (SEQ ID NO:6).

3. The method of claim 1, wherein the antibody is a humanized antibody.

4. The method of claim 1, wherein the antibody is a chimeric antibody.

5. The method of claim 1, wherein the antigen-binding fragment is selected from the group consisting of a Fab, a Fab', a F(ab')$_2$ and a Fv.

6. The method of claim 1, wherein the osteoporosis is associated with estrogen deficiency.

7. The method of claim 6, wherein the estrogen deficiency is associated with menopause.

8. The method of claim 1, wherein the osteoporosis is associated with androgen deficiency.

9. The method of claim 1, wherein the antibody that specifically binds to IL-20 or the antigen binding fragment thereof is administered in combination with another therapeutic agent.

10. The method of claim 9, wherein the other therapeutic agent is a TNFα antagonist.

11. The method of claim 10, wherein the TNFα antagonist is selected from the group consisting of an etanercept polypeptide, infliximab and adalimumab.

12. The method of claim 9, wherein the another therapeutic agent is an IL-20 R1 antagonist, an IL-20 R2 antagonist, or an IL-22 R1 antagonist.

13. The method of claim 12, wherein the IL-20 R1 antagonist is an anti-IL-20 R1 antibody, the IL-20 R2 antagonist is an anti-IL-20 R2 antibody, and the IL-22R1 antagonist is an anti-IL-22R1 antibody.

* * * * *